United States Patent
Mills, Jr. et al.

(10) Patent No.: US 6,741,956 B1
(45) Date of Patent: May 25, 2004

(54) ANALOG COMPUTATION USING HYBRIDIZATION-CAPABLE OLIGOMERS

(75) Inventors: Allen P. Mills, Jr., Chatham, NJ (US);
Bernard Yurke, Plainfield, NJ (US);
Philip M. Platzman, Short Hills, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/129,958

(22) Filed: Aug. 6, 1998

Related U.S. Application Data

(63) Continuation-in-part of application No. 09/078,761, filed on May 15, 1998, now Pat. No. 6,150,102, which is a continuation-in-part of application No. 09/018,248, filed on Feb. 3, 1998, now Pat. No. 6,083,726.

(60) Provisional application No. 60/086,654, filed on May 26, 1998.

(51) Int. Cl.[7] .............................. G06G 7/48; G06G 7/58; G01N 33/48; G06F 3/00; C12Q 1/68

(52) U.S. Cl. .................... 703/3; 702/19; 703/11; 703/21; 708/1; 708/100; 710/1; 435/6

(58) Field of Search ................ 703/3, 11, 21; 702/19, 20; 708/1, 100; 710/1; 435/6; 536/24.3, 231

(56) References Cited

U.S. PATENT DOCUMENTS

| | | | |
|---|---|---|---|
| 5,412,087 A | 5/1995 | McGall et al. | 536/24.3 |
| 5,445,934 A | 8/1995 | Fodor et al. | 435/6 |
| 5,503,980 A | 4/1996 | Cantor | 435/6 |
| 5,545,531 A | 8/1996 | Rava et al. | 435/6 |
| 5,605,662 A | 2/1997 | Heller et al. | 422/68.1 |
| 5,804,373 A * | 9/1998 | Schweitzer et al. | 435/6 |
| 5,843,661 A * | 12/1998 | Rothemund | 435/6 |
| 5,955,322 A * | 9/1999 | Guarnieri et al. | 435/91.1 |

FOREIGN PATENT DOCUMENTS

WO    89/10977    * 11/1989

OTHER PUBLICATIONS

Deaton et al, "Reliability and efficiency of DNA based computation", Physical Review Letters 80(2):417–420, Jan. 12, 1998.*
Alan Dove, "From bits to bases: Computing with DNA," Nature Biotechnology, vol. 16, Sep. 1998, pp. 830–832.
Robert Pool, "A Boom in Plans for DNA Computing," Science, vol. 268, A pr. 28, pp. 498–499.
R.J. Lipshutz, et al., "Using Oligonucleotide Probe Arrays . . . ," Biotechniques, vol. 19, No. 3, 1995, pp. 442–447.
Edward L. Sheldon, et al., "Matrix DNA Hybridization," Clinical Chemistry, vol. 39, No. 4, 1993, pp. 718–719.
Charles R. Cantor, et al., Biophysical Chemistry, Part III, W. H. Freeman & Co., San Francisco, CA, 1980, pp. 1217, 1226–1234.

Primary Examiner—Ardin H. Marschel

(57) ABSTRACT

The present invention is directed to an analog, oligomer-based method for determining a mathematical result of carrying out an operation of matrix algebra on input data. The method comprises representing at least one m-component vector $V = \Sigma_i V_i e_i$ by a set of single-stranded oligomers $E_i$ and $\underline{E}_i$ which are in 1:1 correspondence with the basis vectors $e_i$, $i = 1, 2, \ldots, m$ in an abstract m-dimensional vector space. A composition comprising at least one set of oligomers $E_i$ and $\underline{E}_i$ representing the components of a vector is obtained as input date and is subjected to at least one physical or chemical treatment having an effect on the oligomers that is an analog representation of an operation of matrix algebra. The method can be used to represent the operations of a neural network; for example, to produce a content-addressable memory, or a multilayer perceptron.

13 Claims, 8 Drawing Sheets

OTHER PUBLICATIONS

Francisco J. Ayala, et al., *Modern Genetics*, 2d Ed., Benjamin/Cummings Publishing Co., Menlo Park, Ca, 1984, pp. 262–267; Appendix A1–12–A1–14; pp. 672, 687.

James G. Wetmur, "DNA Probes: Applications of the Principles of Nucleic Acid Hybridization," *Critical Reviews in Biochemistry and Molecular Biology*, vol. 26, Nos. 3 & 4, 1991, pp. 227–259.

Hans P. Graf, et al., "Analog Electronics Neural Networks . . . ," *Neural Networks, Concepts, Applications, and Implementations*, vol. I, ed. by V. Milutinovic et al., Prentice–Hall, 1991, pp. 155–179.

D.E. Rumelhart, et al., "Learning Internal Representations by Error Propagation," *in Parallel Distributed Processing: Explorations in the Microstructure of Cognition*, edited by D.E. Rumelhart et al., MIT Press, Cambridge, MA, 1986, pp. 319–363.

James Hutchinson, et al., "Cumputing Motion Using Analog and Binary Resistive Networks," *Computer*, Mar. 1988, pp. 52–63.

Ralph Linsker, "Self–Organization in a Perceptual Network," *Computer*, Mar. 1988, pp. 105–117.

J. Sambrook et al., "Molecular Cloning, A Laboratory Manual," Cold Spring Harbor Lab. Press, Cold Spring Harbor, 1989, pp. 11.2–11.19; 11.45–11.49; 11.52–1.61.

Radoje Drmanac, et al., "Sequencing of Megabase Plus DNA by Hybridization: Theory of the Method," *Geonomics*, vol. 4, 1989, pp. 114–128.

J. Marmur, et al., "Denaturation and Renaturation of Deoxyribonucleic Acid," *Progress in Nucleic Acids Research*, vol. 1, 1963, pp. 231–300.

Roy J. Britten, et al., "Analysis of Repeating DNA Sequences by Reassociation," *Methods In Enzymology*, vol. 29, Part E, 1974, pp. 363–418.

James G. Wetmur, et al., "Kinetics of Renaturation DNA," *J. Mol. Biol.*, vol. 31, 1968, pp. 31, 349–370.

Ted Kamins, *Polycrystalline Silicon For Integrated Circuit Applications*, Kluwer Academic Publishers, Boston, 1988, pp. x–xii, 155–175.

Kurt Kamins, "Multilayer Feedforward Networks . . .," *Neural Networks*, vol. 2, 1989, pp. 359–366.

Leonard M. Adleman, "Molecular Computation of Solutions to Combinatorial Problems", Nov. 11, 1994, Science, vol. 266, pp. 1021–1024.

Richard J. Lipton, "DNA Solution of Hard Computational Problems", Apr. 28, 1995, Science, vol. 268, pp. 542–545.

J.J. Hopfield, "Neural networks and physical systems with emergent collective computational abilities", Apr. 1982, Proc. Natl. Acad. Sci. USA, vol. 79, pp. 2554–2558.

Will Penny et al., "Neural Networks in Clinical Medicine", Oct–Dec. 1996, vol. 16/No. 4, pp. 386–398.

Jerome A. Feldman et al., "Computing with Structured Neural Networks", IEEE ASSP Magazine, Mar. 1988, pp. 91–103.

Bruce D. Shriver, "Artificial Neural Systems" IEEE ASSP Magazine, Mar. 1988, pp. 8–9.

Teuvo Kohonen, The "Neural" Phonetic Typewriter, IEEE ASSAP Mazagine, Mar. 1988, pp. 11–22.

Kunihiko Fukushima, "A Neural Network for Visual Pattern Recognition", IEEE ASSAP Magazine, Mar. 1988, pp. 65–75.

Hans. P. Graf et al., "VLSI Implementation of a Neural Network Model", IEEE ASSAP Magazine, Mar. 1988, pp. 41–52.

Gail A. Carpenter, "The Art of Adaptive Pattern Recognition by a Self–Organizing Neural Network", IEEE ASSAP Magazine, Mar. 1988, pp. 77–88.

Bernard Widrow et al., "Neural Nets For Adaptive Filtering and Adaptive Pattern Recognition", IEEE ASSAP Magazine, Mar. 1988, pp. 25–39.

Frank Guarnieri et al., "Making DNA Add", Science, vol. 273, Jul. 12, 1996, pp. 220–223.

John S. Oliver, "Matrix Multiplication with DNA", J. Mol Evol (1997) 45:161–167.

Eric B. Baum, "Building an Associative Memory Vastly Larger Than The Brain", Apr. 28, 1995, Science, vol. 268, pp. 583–585.

R. Deaton et al., "Reliability and Efficiency of a DNA–Based Computation", Jan. 12, 1998, Physical Review Letters, vol. 80, No. 2, pp. 417–420.

Andrew Marshall et al., "DNA chips: An array of possibilities", Jan. 16, 1998, Nature Biotechnology, vol. 16, pp. 27–31.

Ann Caviani Pease et al., "Light–generated oligonucleotide arrays for rapid DNA sequence analysis", May 1994, Proc. Natl. Sci. USA, vol. 91, pp. 5022–5026.

R. Corn, DNA Computing Overview, http://www.corninfo.chem.wisc.edu/writings/DNAoverview.html, Mar. 13, 1998, pp. 1–3.

R. J. Britten et al., "Repeated Sequences in DNA", Science, Aug. 9, 1968, vol. 161, No. 3841, pp. 529–540.

Graham Ramsay, "DNA chips: State–of–the–art", Nature Biotechnology, vol. 16, Jan. 1998, pp. 40–44.

Chad A. Mirkin et al., "A DNA–based method for rationally assembling nanoparticles into macroscopic materials", Nature, vol. 382, Aug. 15, 1996, pp. 607–609.

Sanjay Tyagi et al., "Multicolor molecular beacons for allele discrimination", Nature Biotechnolgy, vol. 16, Jan. 1998, pp. 49–53.

\* cited by examiner

US 6,741,956 B1

ANALOG COMPUTATION USING HYBRIDIZATION-CAPABLE OLIGOMERS

CROSS-REFERENCES TO RELATED APPLICATIONS

This application is a continuation-in-part of U.S. application Ser. No. 09/078,761 filed May 15, 1998, now U.S. Pat. No. 6,150,102 that issued Nov. 21, 2000, which is a continuation-in-part of U.S. application Ser. No. 09/018,248 filed Feb. 3, 1998, now U.S. Pat. No. 6,083,726 that issued Jul. 4, 2000. This application also claims the benefit of the filing date of U.S. Provisional Application Serial No. 60/086,654 filed May 26, 1998.

FIELD OF THE INVENTION

This invention provides methods for DNA analog representation of vector operations, including vector addition, determination of inner and outer products of vectors, and of the product of a matrix and a vector, using negative as well as non-negative numbers. The methods of the present invention utilize the spectrum of biochemical activities and operations which DNA molecules are capable of undergoing, including base-specific Watson-Crick hybridization, ligation, polymerase extension, site-specific strand cleavage via restriction enzymes, melting of duplex DNA, cleavage of DNA by site-specific endonucleases, and degradation of DNA by exonucleases of broad sequence specificity.

Watson-Crick hybridization of complementary DNA oligomers makes possible a DNA analog representation of highly parallel operations [1, 2]. The present invention develops this potential and provides methods whereby DNA analog representation of the operations of vector algebra is used to produce a DNA-based neural network [3] which may be used in an associative or content addressable memory [4–6] and a DNA multilayer perceptron [7, 8].

BACKGROUND OF THE INVENTION

All publications and patent applications referred to herein are incorporated by reference fully as though each individual publication or patent application was specifically and individually indicated to be incorporated by reference.

Various strategies for finding solutions to mathematical problems have been devised which use sets of DNA oligonucleotides having selected length and sequence properties. For example, there are methods that use DNA oligomers of defined nucleotide sequence to solve a Hamiltonian path problem [1], a "satisfaction" problem [2] and for performing addition [9] and matrix multiplication [10] of non-negative numbers. Baum [11] has proposed using DNA operations akin to those described by Adleman [1] and Lipton [2] to produce an associative DNA memory of enormous capacity. Prior to the development of the methods of the present invention, methods for using DNA oligomers in analog representation of matrix multiplication that include use of negative numbers as well as non-negative numbers were not disclosed or taught.

Adleman [1] first pointed out that Watson-Crick hybridization of complementary DNA strands makes possible a representation of highly parallel selective operations that could be a basis for molecular computation. In practice, small departures from the ideal selectivity of DNA hybridization can lead to undesired pairings of strands that create significant difficulties in implementing schemes using interactions of DNA oligomers to represent large scale Boolean functions. Recently, however, Deaton et al. [12] showed that it should be possible to find a large enough set of mutually non-hybridizing DNA strands to allow digital molecular computation of high complexity with tolerable error rates.

A neural network is a physical system that models a simple biological neuronal system, in that it comprises a large number of interconnected processing elements, called neurons. The activity of a given neuron is determined by the weighted sum of all of the signals that the neuron receives from the neurons to which it is connected. In most neural network models, the total activity of the ith neuron, called a "perceptron," is $$a_i = w_{i0} + \Sigma W_{ij} x_j$$

where $x_j$ is the signal received from the jth neuron that is weighted by an amount $W_{ij}$. $w_{i0}$ is a bias weight, and is usually negative. The ith neuron responds to incoming signals by itself sending a signal $y = F(a_i)$. The function $F(a_i)$ is a saturating function; a common choice is the non-linear logistic or sigmoid function, $$F(a) = (1 + \exp(-a))^{-1}$$

which restricts the output to be between 0 and 1, and gives an approximately linear response for small levels of activity. Thus, the activity of the ith perceptron is positive when the sum of the incoming weighted signals is larger than the negative bias weight; and when the incoming signal is sufficiently large, the output of the ith perceptron is approximately 1 (see, for example, W. Penny et al., page 386–387, in [8]). From the parallel operations and interactions of the neurons emerge collective properties that include production of a content-addressable memory which correctly yields an entire memory from any subpart of sufficient size [3]. Neural networks do not need the high precision associated with digital computing [3]. Because they are fault tolerant, such neural networks can be represented by DNA with the massive parallelism first envisioned by Adleman [1].

BRIEF SUMMARY OF THE INVENTION

The present invention provides a method for DNA-based analog representation of the operations of vector addition and vector and matrix algebra, using negative as well as non-negative numbers, wherein a subset of all single-stranded DNA n-mers is in 1:1 correspondence with the basis vectors $e_i$, i=1,2, ..., m, in an abstract m-dimensional vector space; an m-component vector V in a space with basis vectors $e_i$, i=1 through m, is represented by the equation $V = \Sigma_i V_i e_i$, and its analog representation is a DNA sample containing strands $E_i$ or their complement $\underline{E}_i$, for each i=1 through m, where the presence of $E_i$ or $\underline{E}_i$ is determined by the sign of the amplitude $V_i$ of the ith component of the vector, and the concentration of each $E_i$ or $\underline{E}_i$ is proportional to the magnitude of the amplitude $V_i$.

The present invention further provides a method for implementing an analog neural network, wherein the data of the processing units, or neurons, is in the form of m-component vectors $V = \Sigma_i V_i e_i$, each of which is represented by a set of the oligomers as described above. The interconnections and the transmission of signals between the neuronal units are represented by biochemical processes and reactions involving the oligomers $E_i$ and $\underline{E}_i$; such processes and reactions include diffusion, molecular recognition, and specific hybridization of complementary oligomers, and nucleotide sequence-specific reactions of nucleic acid-modifying enzymes acting on the oligomers, as occur in analog operations of vector addition and vector and matrix algebra. Application of a saturating function to a signal from one or more neuronal units to produce an output is represented by hybridization of a set of oligomers selected by said set of biochemical reactions to a complete, sub-stoichiometric set of single-stranded $E_i$ and $\underline{E}_i$ oligomers, and an output of the neural network is represented by a set of oligomers that specifically hybridize to said sub-stoichiometric set of $E_i$ and $\underline{E}_i$ oligomers.

In a specific embodiment, an analog content addressable memory is produced by representing elements of memory as m-component vectors $V=\Sigma_i V_i e_i$; wherein items of experience, a set of vectors $V_i^a$, are stored in memory by forming the outer product over all the experience vectors for $i \neq j$:

$$T_{ij} = \Sigma_a V_i^a V_j^a;$$

wherein recall of a particular experience $V_i^b$ imperfectly represented as $U_i^b$ is effected by the algorithm:

$$V_i = S(\Sigma T_{ij} V_j + U_i^b);$$

where the function $S(x)$ is a saturating function such as $$g \cdot \tan h(x),$$

with g being the small-signal gain; and wherein the saturating function $S(X_i)$ is implemented by letting DNA strands representing the vector $X_i$ hybridize to a hybridization oligonucleotide array, and the collection of DNA strands representing the saturated Xs, $S(X_i)$, is obtained by selectively denaturing the duplex molecules in the array containing the $S(X_i)$ strands and collecting the desired set of DNA oligomers.

DETAILED DESCRIPTION OF THE INVENTION

Figure 1:
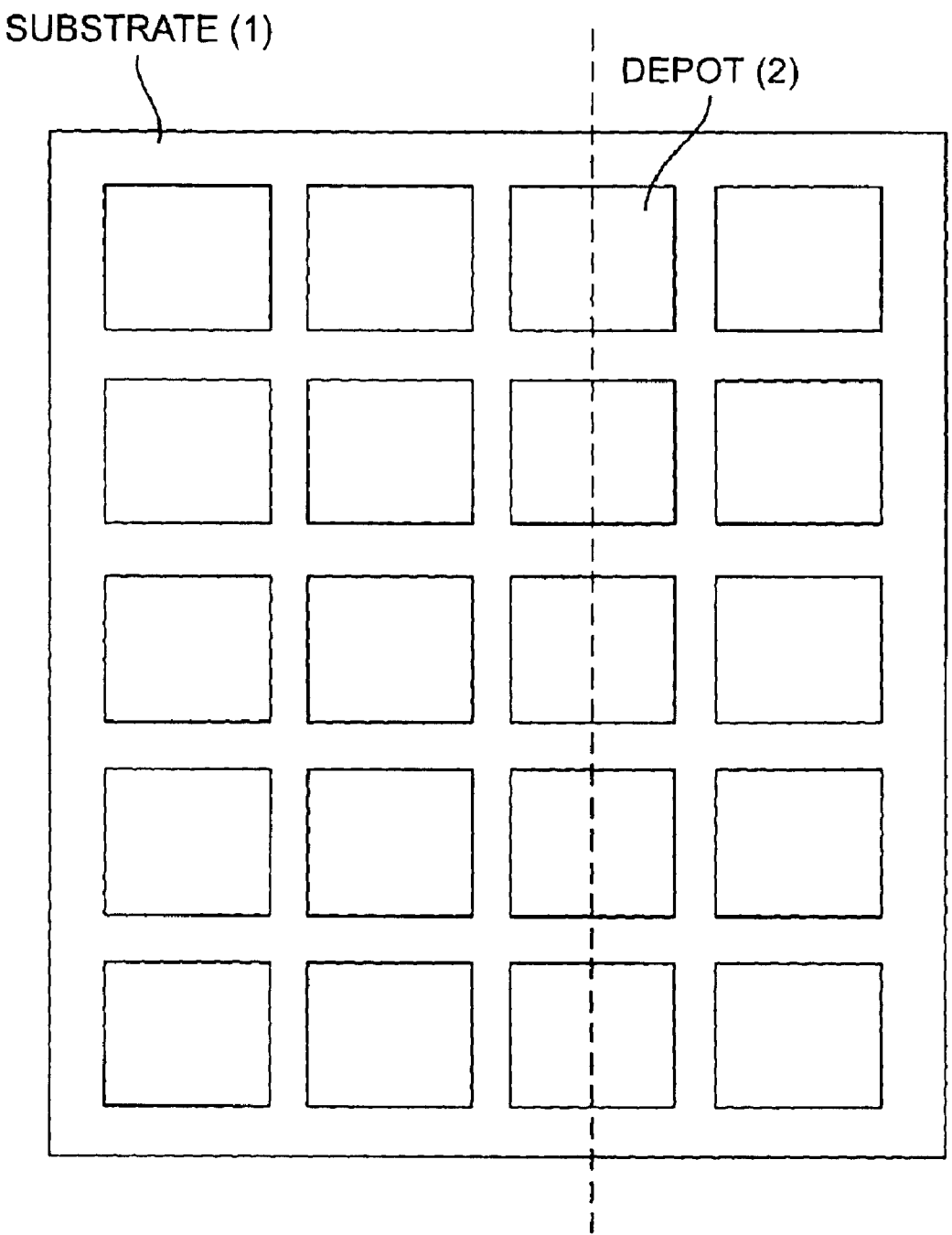
FIG. 1 schematically represents a hybridization array serving as an oligomer-storing device comprising a substrate (1) supporting an array of oligomer depot sites (2). The dotted line indicates the section giving the view shown in FIG. 2.

The present invention employs method steps in which vectors are represented by custom sets of DNA oligonucleotides and/or oligonucleotide analogs having selected subunit sequences, and in which vector operations, including vector addition and vector algebra, are represented in analog form by well known reactions and manipulations of the DNA oligomers representing the vectors, such as hybridization, ligation, and cleavage by nucleases, separation of single-stranded from double-stranded oligomers, and separation of short oligomer fragments from longer oligomers. Unless otherwise indicated, the present invention is practiced using conventional techniques of chemistry, biochemistry, and molecular biology, which are well-known and are within the capabilities of a person of ordinary skill in the art. (for example, see [13]–[18]).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Nucleic Acid Oligomers

Oligomers are linear sequences of relatively few subunits. An oligomer having n subunits is referred to as an n-mer; for example, a nucleic acid oligomer that contains 12 or 17 nucleotides is referred to as a 12-mer or as a 17-mer, respectively. As used herein, the term oligomers refers to RNA or DNA oligonucleotides, RNA or DNA oligonucleotide analogs, or a combination of RNA and/or DNA oligonucleotides and RNA and/or DNA oligonucleotide analogs, which are used in representing vectors and matrices, operations involving vectors and matrices, including vector addition and vector algebra, and in implementing a neural network. The RNA or DNA oligonucleotide analogs employed for the present invention can be oligomers in which from one to all nucleotide subunits are replaced with a nucleotide analog to confer desired properties such as increased detectability, increased hybridization affinity, and resistance to degradation by a nuclease. Such oligonucleotide analogs include but are not limited to oligomers comprising 2'-O-alkyl ribonucleotides, phosphorothioate or methylphosphonate internucleotide linkages, peptide nucleic acid subunits, and nucleotides modified by attachment of radioactive or fluorescent groups, groups which intercalate, cross-link or cleave a nucleic acid, or groups which alter the electric charge or hydrophobicity of the oligomers. Methods for making and using oligonucleotides and oligonucleotide analogs such as those listed above are well known to those skilled in the art of making and using sequence-specific hybridizing oligomers.

In general, an essential characteristic of the oligomers employed in practicing the invention is that they are able to hybridize specifically to oligomers having complementary subunit sequences to form stable double-stranded complexes. The statement that an oligomer hybridizes specifically to another oligomer is intended to mean that a portion of a first oligomer comprising a nucleotide sequence complementary to a sequence in a second oligomer binds by Watson-Crick base-pairing to the complementary portion of the second oligomer to form a stable double-stranded complex, under hybridization conditions that are sufficiently stringent that oligomer molecules having fewer bases complementary to, or forming less stable duplex structures with, the second oligomer do not also hybridize to the second oligomer and form stable double-stranded complexes. Selection of parameters such as the lengths of the complementary portions of the different oligomers and the conditions used in hybridization and wash steps, so that the oligomers hybridize specifically to their counterparts, is well within the capabilities of a person of ordinary skill in the art (e.g., see chapter 11 of [13]).

The sizes of the oligomers employed in practicing the present invention can range from about 4 subunits to 100 or more subunits in length. One skilled in the art would appreciate that in order for the oligomers to hybridize specifically to form stable double-stranded complexes, the oligomers representing basis vectors should be at least about 6–8 nucleotides in length. Depending on the complexity of the data being represented, the basis vectors can be represented by DNA n-mers of from about 8 up to about 20, 30, or 50 or more nucleotides; preferably about 10 to about 30 nucleotides. As discussed below, n-mers representing basis vectors preferably have about 6 to 12 additional nucleotides added to each end to stabilize hybridization of termini, to permit re-separation of oligomers joined end-to end, and to permit amplification by PCR using a common set of primers. Thus, DNA oligomers representing basis vectors are typically about 18 to about 74 or more nucleotides in length; preferably about 20 to about 50 nucleotides in length. In the methods involving hybridization of basis vector oligomers to oligomers attached to a substrate, the basis vector oligomers can be longer, shorter, or the same length as the attached oligomers. In addition, basis vector oligomers having different lengths, chemical structures and properties, can be hybridized to different sites of the same oligomer array. Those skilled in the art appreciate that the specificity and affinity with which oligomers hybridize to each other are determined, in large part, by the length, nucleotide sequence, and chemical structure of the oligomers, and so are able to select structural parameters of the oligomers employed in the present invention that are appropriate for their intended use. For example, the subunit sequences of the different basis vector oligomers and of oligomers attached to solid substrates can be selected so that the oligomers do not comprise self-complementary sequences that stabilize folding of said oligomers into hairpin structures which interfere with formation of inter-strand duplexes. Additionally, the subunit sequences of the oligomers can be selected so that the melting temperatures (Tm) of the double-stranded complexes formed by hybridization of the complementary portions of the basis vector oligomers and the attached oligomers at the different sites of the array are all within a selected temperature range, e.g., in the range of a selected Tm plus or minus about 5 degrees C., for more efficient control of oligomer hybridization and release.

Obtaining the Oligomers

The present invention employs multiple sets of large numbers of different oligomers, for example, DNA oligonucleotides, having specified lengths and nucleotide sequences. The oligomers of the present invention can be made by well-known methods that are routinely used by those skilled in the art of synthesizing oligonucleotides and/or oligonucleotide analogs (for example, see [16, 17, and 19]).

An Oligomer Storing Device

In the preferred embodiments of the invention, the required oligomers are synthesized and stored in an oligomer storing device, from which they are released as they are needed. A preferred oligomer storing device comprises a substrate supporting an array of oligomer storage sites, or depots, each of which comprises a surface to which are attached oligomers having a selected subunit sequence. The oligomers are stored in the depots of the storing device by allowing them to hybridize by Watson-Click pairing to the oligomers attached to the surfaces of said depots to form double-stranded complexes. When oligomers having a particular nucleotide sequence are needed, they are released from the oligomer storing device by locally denaturing the double-stranded complexes of the depot in the storage array where they are stored, e.g., by localized heating, without denaturing double-stranded complexes of the depots storing other oligomers, and the desired oligomers are collected from the solution in contact with the oligomer storage array.

The substrate supporting the array of oligomer storage sites, or depots, can have a flat surface that supports the array, or it can be distributed in three dimensions, such as in a gel, a fibrous or granular matrix, or in a porous solid. A substrate which is suitable for supporting immobilized nucleic acids for hybridization analysis can, in general, be adapted for use as an oligomer storage device of the present invention. Accordingly, a variety of different designs and materials are available for preparing the oligomer storing device of the present invention. For example, the storage device may be a flexible filter, e.g., of nylon or nitrocellulose, or it may be of a rigid material such as silica, silicon, glass, crystalline $Al_2O_3$ ("synthetic sapphire"), beryllium oxide, or a solid substrate coated with a noble metal such as gold. Methods for making such substrate supports for hybridizing oligomers are well known to those skilled in the art (see [20] col. 6, lines 1–39; [21] col. 11, lines 49–63; [22] col.9, line 10, to col. 32, line 7; [23] pages 40–42; [24] pages 114–128; 8 25] pages 607–609, and [26]). The storage device may also include a chamber or container housing the substrate, through which oligomer hybridization, wash, and collection solutions are directed, for convenience of use similar to that of a chromatography column.

Figure 2:
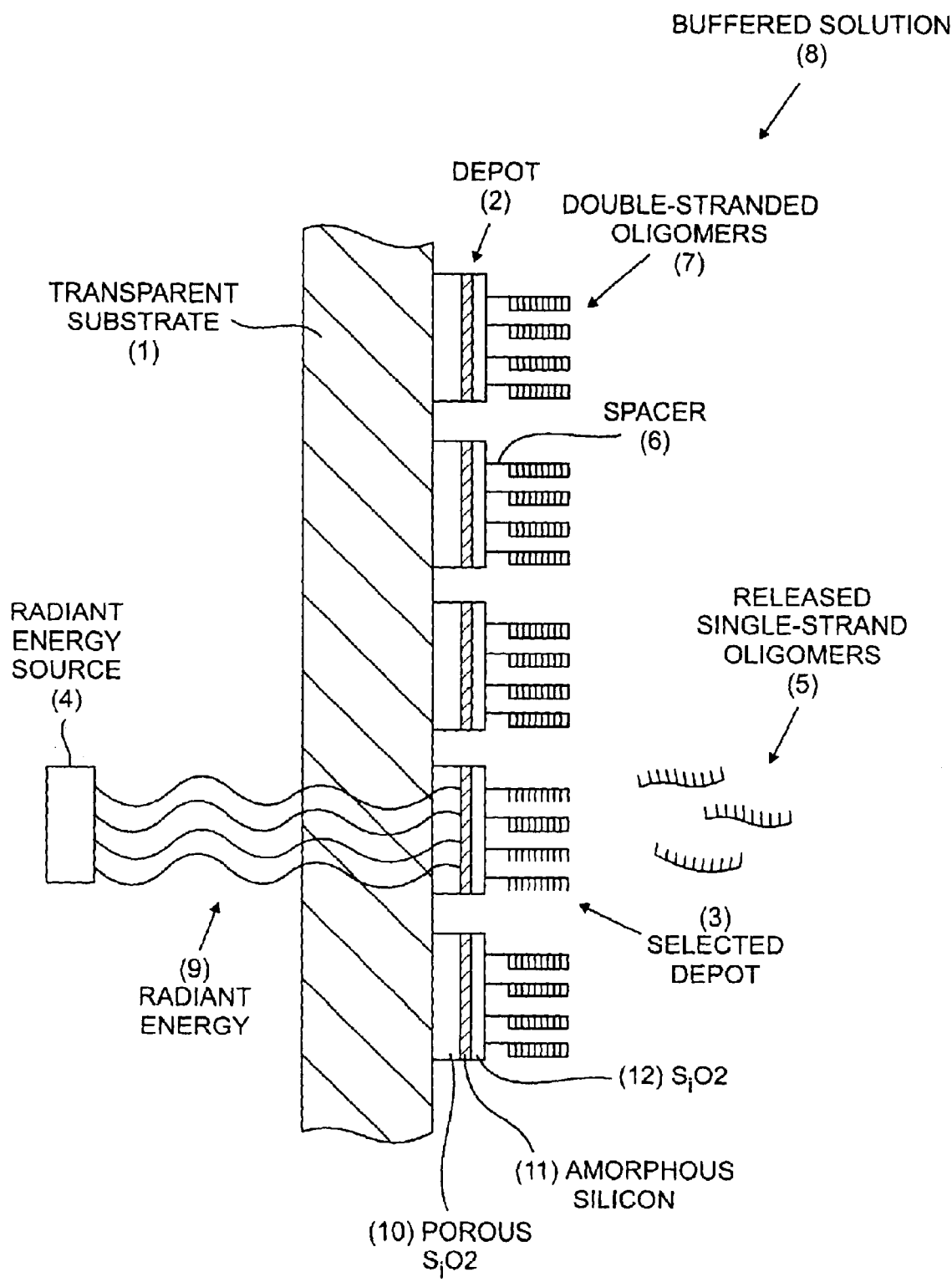
FIG. 2 schematically represents a cross-section through a row of depot sites of the oligomer-storing device shown in FIG. 1, for which the substrate (1) is a transparent substrate. A preferred embodiment of the present invention is shown wherein localized heating of a selected depot (3) is achieved by using a source of radiant energy (4) to irradiate the selected depot site through the transparent substrate (1) to release the desired single-stranded oligomers (5).

The term depot refers to a site at which oligomers are stored, and comprises a delimited area or volume that is part of or is attached to the supporting substrate, to the surface of which are attached hybridizing oligomers comprising a selected subunit sequence (for example, see (2) in FIGS. 1 and 2). A depot site can have any size, shape, or volume, consistent with the objective of the invention of storing and selectively releasing oligomers as needed. By array is meant an arrangement of locations, or depots, in or on the supporting substrate of the oligomer-storing device. The depots can be arranged in 2- or 3-dimensional arrays, or other matrix formats. FIG. 1 shows a 2-dimensional 4×5 array of depots on a supporting substrate. The number of depots in the array can range from 2 to $10^7$ or more. It is within the knowledge of those skilled in the art to fabricate a rigid substrate supporting an array of oligomer depot sites that can range in diameter from about 1 micron to 1 centimeter or more, and an array of depot sites of 5–10 microns in diameter can readily be made with an array density of about $10^6$ depot sites per $cm^2$ (see [20] col. 8, lines 50–68; [21] col. 9, lines 10–18; and [23] page 40). All of the depot sites of a given array can have the same diameter, or a single depot array can comprise depot sites having different diameters. Preferably, the oligomer storing device stores $10^2$ to $10^7$ different types of oligomers of about 6 to about 100 subunits in length in a micro-array of thermally isolated depot sites on a rigid substrate.

The oligomers attached at the depot sites can be attached directly to the surface of the substrate, or to the surface of a pad or pedestal-like structure that is itself attached to the substrate, and which is made of material that is the same as, or different from, that of the substrate. The depot surface to which the oligomers are attached can be located on a raised feature or in a well-like depression on the surface of the supporting substrate. FIG. 2 shows oligomers attached to a depot site (2) comprising a raised pad comprising three different layers ((10), (11), and (12)) affixed to a rigid transparent substrate (1).

Methods for making arrays comprising oligomers attached at depot sites to produce oligomer-storing devices for the present invention are well known. Such methods include in situ synthesis of oligomers attached at their 3' ends to a functionalized surface such glass, $SiO_2$, or GaAs (for example, see [20] col. 4, line 67 to col. 10, line 35; [21] col. 23, line 3, to col. 25, line 18; and [22] col. 17, lines 21–63). Alternatively, pre-synthesized oligomers can be chemically attached to the substrate, e.g., by derivatizing the oligomers or the attachment surface, and then depositing microdroplets of the oligomers at the appropriate depot sites and allowing the oligomers to react with the depot site surface, or by attaching biotinylated oligomers to a streptavidin-coded surface (see [20] col. 1, line 18 to col. 3, line 13 and col. 6, line 21 to col. 10, line 35; [25] pages 607–609; [27] col. 13, lines 2–9; and [28] pages 27–29). Preferably, the oligomers are attached to the depot sites through uncharged spacer groups ((6) in FIG. 2) that tether one end of each of the oligomers to the depot surface ([22] col. 11, line 49, to col. 13, line 45; and [29] pages 5022–24), since the use of such spacer groups is known to increase hybridization efficiency ([28] page 29).

Storing Soluble Oligomers in a Depot Array

Oligomers are stored in the depot array of a storage device by allowing them to hybridize specifically to oligomers comprising complementary subunit sequences which are attached at the depot sites ((2) in FIG. 2), to form double-stranded oligomer complexes attached to the depot sites ((7) in FIG. 2). Those skilled in the art recognize that the number of consecutive complementary nucleotides that must be present in an oligonucleotide so that it hybridizes specifically to a target nucleic acid molecule can vary considerably, from about 4 up to 14 or more, depending on such factors as the complexity of the set of target nucleic acids and the physical conditions (ionic strength, temperature, anionic and cationic reagents, etc.) used in the hybridization and wash steps. A complete set of oligonucleotides comprising every possible sequence of n consecutive nucleotide subunits can be stored in an array of $4^n$ depot sites comprising complementary oligomers by exposing the array to a solution containing the soluble oligomers at a sufficiently low temperature, in a suitable buffer containing a high molar concentration of a monovalent cation such as $Na^+$. The time required to saturate the $4^n$ depot sites with the $4^n$ different n-mer oligomers depends on the concentrations of the oligomers, the temperature, and the concentration of $Na^+$ ions. If the soluble oligonucleotides are applied at a nucleotide concentration of 0.5 mole per liter under conditions favorable for hybridization, the time for half of the hybridization reaction to be completed is about 36 seconds for n=10, and about 16 hours for n=15 [30–33].

Releasing Selected Oligomers

A custom set of soluble oligomers of known composition is obtained by locally denaturing double-stranded complexes of selected depots of the intact array comprising the desired oligomers, and collecting the oligomers released from the selected depots ((5) in FIG. 2) into the buffer solution in which the array is immersed ((8) in FIG. 2). Denaturation of oligomer complexes at selected depots can be achieved by any of the nucleic acid-denaturing treatments known to those skilled in the art of nucleic acid biochemistry. Those skilled in the art appreciate that the melting temperature of a double-stranded oligonucleotide complex is dependent on the length, nucleotide sequence, and chemical structure of the complex, and on the ionic strength and chemical composition of the solvent (see [13] page 11.46).

The preferred method for denaturing double-stranded complexes at the selected depots to release the desired oligomers is by locally heating the selected depots so as to subject the selected depots to a raised temperature under appropriate solution conditions for a period of time sufficient to release the desired oligomers from the selected depots. Localized heating of the selected depot surfaces can be achieved by any suitable means in accord with the structure and size of the supporting substrate, and the size and disposition of the individual depot sites. For example, selected depots can be locally heated by illuminating the surface of the array, in a suitable buffer and at a temperature below the melting point of the oligomer duplexes, with a pattern of focused irradiation from a radiant energy source ((4) and (9) in FIG. 2), e.g. an argon laser, that heats only those depots storing the desired oligomers. The laser can be mounted on a support which provides precise x-y translation control, to permit controlled heating of one depot at a time, in serial fashion. Alternatively, the laser can have a broad beam that can irradiate a mask, the image of which can irradiate all of the depots in the array at once. The mask is used to shield the unselected depots so that only those depots containing the desired oligomers are heated. To heat a single depot having a surface area of about 100 $\mu m^2$ to about 70° C. in a suitable buffered solution so as to locally melt double-stranded DNA duplexes stored at the heated depot will require roughly 10 milliwatts of argon laser light (488 nm). In the preferred method, a substrate which is transparent to argon laser light, e.g. crystalline $Al_2O_3$, is used to support thermally isolated, light-absorbing, depot surfaces to which the oligomers are attached, allowing back illumination of the desired depots as shown in FIG. 2, and protecting the oligomers from direct exposure to the laser radiation. A substrate of $Al_2O_3$ is also suitable because its relatively high thermal conductivity permits the substrate to act efficiently as a heat sink, drawing heat away from the irradiated depot sites and so providing greater thermal isolation of the unselected depot sites. Alternatively, the storage device substrate comprising the depot array could be in contact with, or have integrated within it, a controllable, addressable, array of resistive heating elements which is spatially aligned with the depot array, so that application of current to selected resistive heating elements locally heats selected depots proximal to the activated heating elements to release the desired oligomers. Heller et al. teach fabrication of a silicon substrate into which is integrated a micro-array of electronically addressable micro-locations corresponding to a micro-array of DNA storage sites ([22] col. 9–10, 12–16). Accordingly, it is within the knowledge of those skilled in the art of microlithography and thick film circuitry to fabricate a DNA chip in which there is integrated an array of electronically addressable micro-locations comprising resistive heating elements such as can be formed, for example, by depositing undoped polycrystalline silicon at positions between addressable conducting wire grids [34]. As described by Heller et al., metal contact pads along the outside perimeter of the chip permit the wiring of such a chip comprising an integrated, electronically addressable, micro-array to a microprocessor-controlled power supply and interface for controlling the device ([22] col. 12). The amounts of oligomers released by localized heating can be controlled by varying the amount of heat applied, e.g., by controlling the intensity of the laser light or the temperature of the resistive heater, and/or by varying the time period during which heat is applied. According to the preferred method, the localized heating of selected depots to release desired oligomers stored therein is electronically controlled by a programmable microprocessor and an interface for controlling the process. Local heating of selected depots, will cause oligomer duplexes at the heated depots to melt in a short time, of the order of seconds, to yield single-stranded oligomers in quantities related to the time and extent of heating.

Heller et al. teach that denaturation of DNA at selected depots can also be induced by locally increasing the negative electric potential at the selected depots ([22] column 20). In addition positively charged chaotropic agents and other denaturants can be added to the solution in contact with the selected depots to promote denaturation of the attached double-stranded complexes. Exposure to denaturing solution conditions can be limited to the depots selected for denaturation by surrounding the selected depot surfaces with a liquid-impermeable barrier that prevents the denaturing solution from contacting non-selected depot surfaces. For example, individual depots of a large-scale array, in which depot surfaces are 0.1 to 10 mm or more in diameter, can be situated in wells or surrounded by raised divider walls to be fluidically isolated from each other, so that selected depot surfaces can be exposed to denaturing solution without also exposing non-selected depot surfaces to the denaturing conditions. Denaturation of selected depots, whether by localized heating, application of increased negative potential, denaturing solution, or any combination of these means, can be carried out serially, one depot at a time, or in parallel with multiple depots being treated simultaneously.

Collecting the Released Oligomers

Oligomers released from selected depot sites following denaturation of double-stranded complexes at those sites ((5) in FIG. 2) are collecting by collecting the solution in contact with the treated depot surfaces ((8) in FIG. 2). The solution in contact with the oligomer-storing depot array can be enclosed or contained within a reservoir, and once the desired oligomers are released into the solution, it can be collected by any suitable means, e.g. by a manually operated or automated pipetting device, or a syringe. Alternatively, the solution containing the desired oligomers can be removed from the reservoir and transferred to a suitable collecting device, and fresh solution can be added to the reservoir in its place, e.g. to wash away residual oligomers in preparation for releasing a different set of oligomers, by using automated or microprocessor-controlled pumps that direct the flow of the different solutions through tubes connected to the reservoir.

Refreshing Vector Operations With DNA Oligomers

The DNA-based analog methods of the present invention permit one to carry out operations of vector addition and vector and matrix algebra, including determining the inner and outer products of two vectors, determining the product of a matrix and a vector, and determining the product of two matrices.

Vectors

Any m-component vector V in a space with basis vectors $e_i$, i=1,2, . . . , m is represented by the equation $$V=\Sigma_i V_i e_i \quad (1).$$

A subset of all single-stranded DNA n-mers is selected to be in 1:1 correspondence with the basis vectors $e_i$, i=1,2, . . . , m in an abstract m-dimensional vector space. The analog representation of V is then a DNA sample containing strands $E_i$, with the concentration of each strand $[E_i]$ being proportional to the amplitude $V_i$ of the i-th component of the vector. For example, a typical 10-mer, $E_i$=5' AGCTATCGAT 3'(SEQ. ID NO:1) can be associated with the basis vector $e_i$ identifying one direction in a space of at most $4^{10}=10^6$ dimensions. The analog accuracy of representing a vector V in this manner will be limited by Poisson fluctuations in the numbers of molecules in a finite sample volume; roughly 1 pmole of DNA oligomers would represent a random vector for m=$10^8$ with roughly 1% errors in the individual amplitudes.

Since DNA concentrations are always positive, an appropriate representation for negative amplitudes is needed [10]. In the present invention, negative amplitudes associated with unit vectors $e_i$ are represented by DNA oligomers $\underline{E}_i$ having a nucleotide sequence complementary to $E_i$. As a result, when two vectors are added, any positive and negative amplitudes will hybridize, and the resulting double-stranded DNA oligomers can be removed from the set of single-stranded DNA molecules; for example, by digestion with a suitable enzyme, or by column separation.

The nucleotide sequences of the DNA oligomers of the present invention, and the conditions for their reaction, are selected to optimize interactions between the DNA oligomers that are analog representations of the vector and/or matrix operations of interest. For example, the n-mers can be synthesized with an invariant r-mer $R_1 R_2 \ldots R_r$ at their 5' ends, and an invariant r-mer $S_1 S_2 \ldots S_r$ at their 3' ends, with r independently being about 3–6, to assist in hybridization reactions involving n-mer termini which are employed in representing operations such as determination of the inner product of vectors V and W, as described below. Additionally, the DNA n-mers can be synthesized to have one half of a palindromic restriction enzyme recognition sequence at each end, to permit cleavage that separates pairs of strands that have been joined end-to-end for operations such as determination of the product of a matrix and a vector, also as described below. To prevent introduction of error into the operations by undesired interactions between DNA oligomers which are not fully complementary, the nucleotide sequences of the DNA n-mers are preferably selected so that the DNA n-mers are non-palindromic, relatively free of hairpin effects, and have minimal overlap with the other basis vectors [12].

A suitable choice for a set of n-mers having structures which are useful for the present invention is a set of single-stranded (q+2r+6)-mers of the form:

$$E_i=5'\ TAC\ R_1R_2 \ldots R_r\ N_1^i N_2^i N_3^i \ldots N_q^i\ S_1S_2 \ldots S_r\ GTA\ 3'(2),$$

where the core sequence $N_1^i \ldots N_j^i \ldots N_q^i$ of length q nucleotides is associated with the basis vector $e_i$. When such strands are joined end-to-end, the nucleotides at the junction form a palindromic restriction enzyme recognition sequence having the sequence 5' GTATAC 3', which, when hybridized to its complement to form a double-strand, is cut in the center by the restriction enzyme Bst1107 I [35]. Negative amplitudes associated with unit vectors $e_i$ are represented by the sequence of bases complementary to $E_i$, e.g.

$$\underline{E_i}=5'\ TAC\ \underline{S_r} \ldots \underline{S_2S_1N_q^i} \ldots \underline{N_3^iN_2^iN_1^i}\ \underline{R_r} \ldots \underline{R_2R_1}\ GTA\ 3'\ (3).$$

Since each nucleotide of the core q-mer is chosen from the four bases A, G, C, T, the number of such sequences is $4^q$. If $4^q \gg m$, it is possible to select a subset of q-mers which will give a set of basis vector strands that are non-palindromic, relatively free of hairpin effects and have minimal overlap with the other basis vectors [12].

Addition of Vectors

Addition of two vectors can be carried out as follows:

(I) Equal quantities from the two collections of DNA representing the two vectors, at twice the standard concentration, are combined under solution and temperature conditions that allow only fully complementary n-mer strands to hybridize to form stable double-stranded DNA complexes. Positive and negative contributions to the concentration of oligomers corresponding to any given basis vector hybridize to yield double-stranded DNA with blunt ends. After the reaction is complete, the positive and negative type DNA n-mers for each basis vector which remain as single-stranded oligomers represent the sum of the two vectors.

(II) The double-stranded DNA oligomers are separated from the single-stranded DNA n-mers of the same length by a high-performance liquid chromatography (HPLC) purification step. Alternatively, double-stranded DNA oligomers can be separated from the single-stranded ones by digesting the DNA with an appropriate enzyme such as Exonuclease III (*E. coli*), that cleaves double-stranded DNA but not does not cut single-stranded DNA [36]. Following digestion of the DNA with Exonuclease III, the reaction mixture contains the single-stranded DNA oligonucleotides, plus unwanted DNA fragments that are significantly shorter than the DNA strands representing the vectors. The set of intact single-stranded DNA oligomers is then purified; for example, by HPLC, or by gel electrophoresis and elution of the DNA from the gel. The set of intact single-stranded DNA oligomers obtained after mixing the two DNA sets and removing the double-stranded DNA molecules as described above is an analog representation of the sum of the two vectors. The sum of any number of vectors can be taken simultaneously in the same manner. Multiplication of any of the individual vectors by a scalar is represented by adjusting the concentration of the DNA molecules corresponding to that vector.

Inner Product of Two Vectors

The inner product of two vectors $\Sigma_i V_i W_i$ can be found as follows:

(I) Three separate samples of each of the two collections of DNA n-mers representing the individual vectors $V_i$ and $W_i$ are obtained.

(II) A first pair of samples of the $V_i$ and $W_i$ vectors is combined and the rate of hybridization, $R_-$, is measured. The value of $R_-$ is proportional to the time rate of increase of V-W duplex strands representing quantities of opposite sign. The individual contributions to $R_-$ are proportional to the product of the concentrations of the two V and W strands, and. hence are proportional to the inner product. The concentration of double-stranded DNA is measured, e.g., by treating the DNA mixture with a fluorescent dye such as ethidium bromide that intercalates the double helix. The DNA-ethidium bromide complex fluoresces at 590 nm when excited by 300-nm light, and thus provides a quantifiable signature for the concentration of double stranded DNA.

(III) A V sample and a W sample are each treated to modify the 3' ends of the strands so that additional nucleotides cannot be attached in a polymerase-catalyzed extension reaction. For example, dideoxy-nucleotides can be added to the 3' termini of the V and W strands in a reaction catalyzed by a terminal transferase. Alternatively, a short oligomer having a non-extendable nucleotide (e.g., a dideoxynucleotide) at its 3' end can be ligated to the 3' ends of the V and W strands, using bridging linker oligomers, followed by separation of the modified V and W strands from the shorter oligomers.

Figure 3:
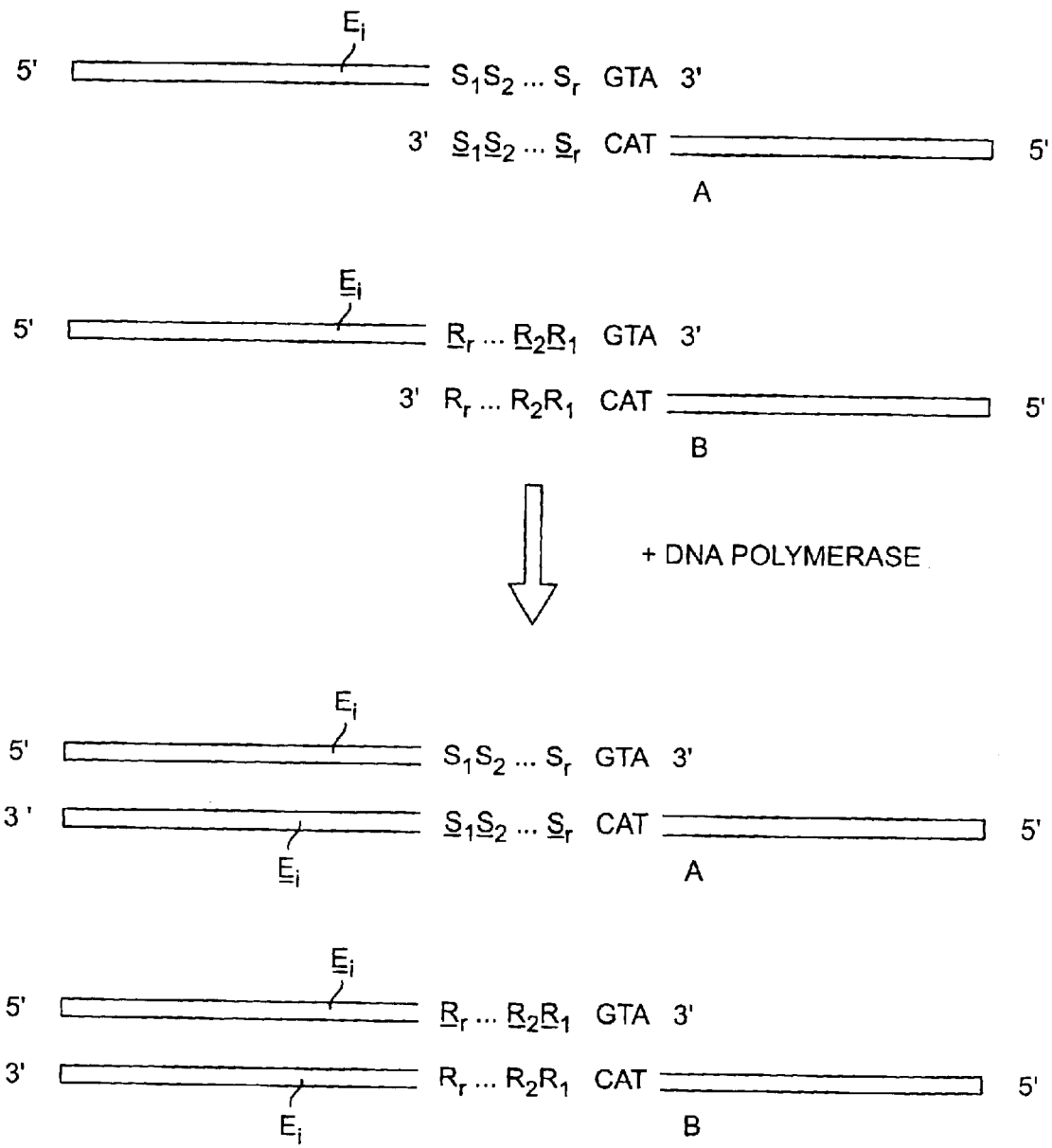
FIG. 3 schematically represents steps in the determination of the inner product of V and W in which primers A and B are hybridized at their 3' ends to the 3' ends of the DNA strands of vector V or W, and the 3' ends of the primer strands are extended to produce DNA strands $\underline{V}$ or $\underline{W}$ that are complementary to the V or W template strands.

(IV) The modified V and W strands are each incubated separately with DNA polymerase in a suitable buffer and the two primers, 5' AATGCAAGATCGAAATTTATACGTTTATCT TAC $\underline{S_r}\ldots\underline{S_2}$
  $\underline{S_1}$ 3' (SEQ ID NO: 2)                                                 (A), and 5' AATGCAAGATCGAAATTTATACGTTTATCT TAC $R_1R_2\ldots$
  $R_r$ 3' (SEQ ID No:3)                                                 (B), where 5' AATGCAAGATCGAAATTTATACGTT-TATCT 3' (SEQ ID NO:3) exemplifies a long, inert strand that does not hybridize with any of the $V_i$ or $W_i$ strands and form a stable double-stranded complex under the conditions used in the subsequent reaction steps. Of course, primer strands having other nucleotide sequences that do not hybridize with any of the $V_i$ or $W_i$ strands can be used instead of those shown above as (A) and (B), with equal success. The 3' ends of the long primer strands are extended on the V and W templates, producing the complements $\underline{V}$ and $\underline{W}$ to all the V and W strands present (FIG. 3).

(V) The $\underline{V}$ and $\underline{W}$ complementary DNA oligomers produced by extension of the long primers (A) and (B) are separated from the shorter V and W template strands by HPLC to yield the $\underline{V}$ and $\underline{W}$ strands.

(VI) The third pair of samples of V and W DNA strands is used in combination with the $\underline{V}$ and $\underline{W}$ strands obtained in the previous step to measure the rate of hybridization $R_+$. V strands are mixed with $\underline{W}$, and $\underline{V}$ with W, and the rate of hybridization $R_+$ is measured for each reaction. The value $R_+$ should be the same for each reaction; when the two rates may differ, e.g., due to effects of sequence-dependent oligomer structure on the average melting temperature of each strand mixture, the average of the two rates can be obtained and used as $R_+$.

(VII) The inner product of the two vectors is represented by the suitably normalized difference of the rates, $R_+ - R_-$, where each rate $R_+$ and $R_-$ is suitably normalized to correct for concentration differences.

Outer Product of Two Vectors

The outer product matrix $V_i W_j$ is formed by joining the 3' ends of the single-stranded DNA oligomers corresponding to $V_i$ to the 5' termini of the DNA oligomers corresponding to $W_j$.

(I) To ensure that the $V_i$ and $W_j$ strands are attached to each other in the proper orientation, the 5' phosphate residues are removed from the $V_i$ oligomers, e.g., using bacterial alkaline phosphatase, and the 5' termini of the $W_j$ are phosphorylated, e.g., using bacteriophage T4 polynucleotide kinase.

(II) The $W_j$ strands are further modified by ligating to their 3' termini a long, inert strand $\{F\}$ that does not hybridize with any of the $V_i$ or $W_j$ strands and form a stable double-stranded complex under the conditions used in the subsequent reaction steps. The modified $W_j$ strands and the $\{F\}$ strands are ligated using bridging linker oligomers having the structure:

     (C), and

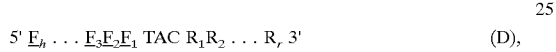     (D), where h is about 6–9, such that the h nucleotides at the 5' ends of the bridging linker strands are complementary to the first h nucleotides at the 5' ends of the $\{F\}$ strands. The bridging linkers (C) and (D) thus hybridize to the 3' terminal portions of the modified $W_j$ strands and the 5' terminal portions of the F strands and align them end-to-end for efficient ligation to obtain strands of the form $\{E_j\}\{F\}$ and $\{\underline{E}_j\}\{F\}$, which are purified from the shorter bridging linker oligomers.

(III) The modified $V_i$ and $W_j\{F\}$ strands are then ligated together using the four types of bridging linker strands:

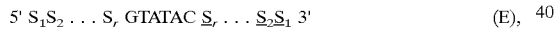     (E),

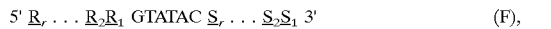     (F),

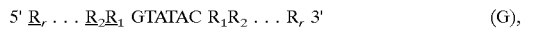     (G), and

Figure 4:
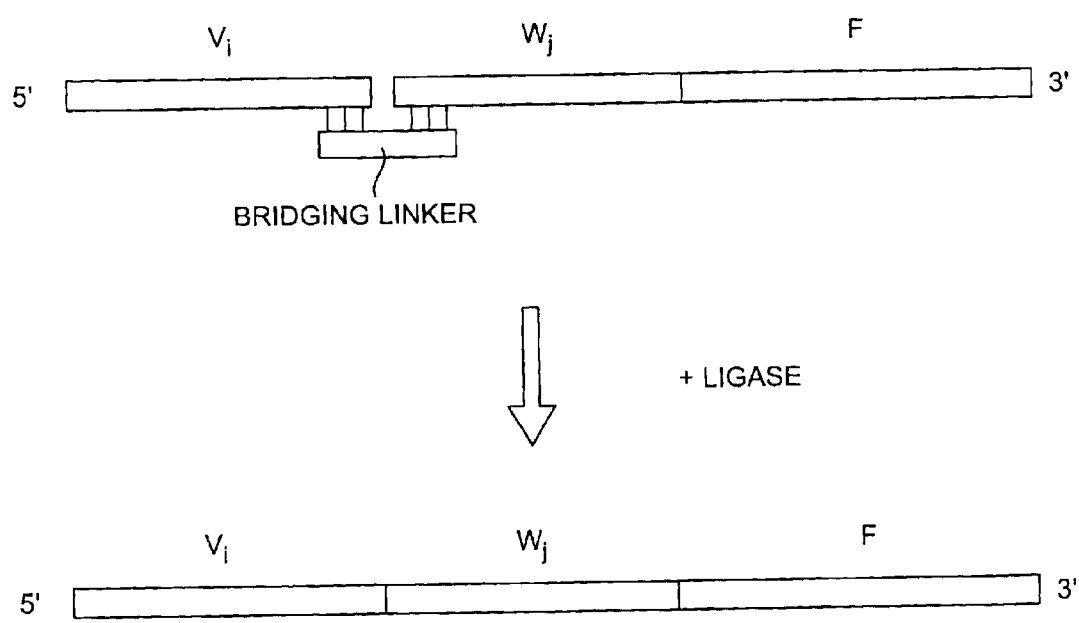
FIG. 4 schematically represents steps in the determination of the outer product of V and W in which a bridging linker oligomer aligns the 3' end of a $V_i$ strand and 5' end of a $W_j\{F\}$ strand for efficient ligation to obtain a strand of the form $\{E_i\}\{E_j\}\{F\}$.

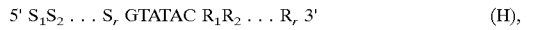     (H), which hybridize to the 3' terminal portions of the $V_i$ strands and the 5' terminal portions of the $W_j$ strands and align them end-to-end for efficient ligation to obtain strands of the form $\{E_i\}\{E_j\}\{F\}$, $\{\underline{E}_i\}\{E_j\}\{F\}$, $\{E_i\}\{\underline{E}_j\}\{F\}$, and $\{\underline{E}_i\}\{\underline{E}_j\}\{F\}$ (FIG. 4). The number of ij strands is proportional to the product of the concentrations of the $V_i$ and $W_j$ strands and hence to the desired outer product. This is approximately true even if the reaction is allowed to run to completion, since there are so many different reactions competing for the same strands. DNA strands of the form $E_i E_i$ will spontaneously form hairpins and may be removed by a first purification stage using gel electrophoresis or chromatography at room temperature. The remaining diagonal components of $T_{ij}$, of the form $E_i E_i$ and $\underline{E}_i \underline{E}_i$ (e.g. $T_{11}, T_{22}, T_{33} \ldots$) may be removed if desired by allowing the strands representing $T_{ij}$ to hybridize with an equal total concentration of strands representing a unit matrix $\delta_{ij}$ having only diagonal components. The desired $T_{ij}$ strands lacking any diagonal components may then be extracted by a second purification stage performed under temperature and solution conditions selected such that single duplex pairs of E's melt, but double length hybridized segments corresponding to $T_{ii} \delta_{ii}$ remain in double-stranded form.

Product of a Matrix and a Vector

This method allows one to find the matrix inner product $\Sigma_j T_{ij} X_j$, given a matrix T represented by strands of the form $\{E_i\}\{E_j\}\{F\}$, $\{E_i\}\{\underline{E}_j\}\{F\}$, $\{\underline{E}_i\}\{E_j\}\{F\}$, and $\{\underline{E}_i\}\{\underline{E}_j\}\{F\}$, and a vector X represented by strands of the form $\{E_i\}$ and $\{\underline{E}_i\}$ having concentrations proportional to the amplitudes $X_i$. The strands $\{E_i\}$ and $\{\underline{E}_i\}$ of vector X will be referred to as $\{X_j\}$ to distinguish them from the strands of the matrix T.

(I) Obtain a sample of the complement to $\{X_j\}$, which is $\{\underline{X}_j\}$.

(II) To the 5' ends of both the $\{X_j\}$ strands and their complements, ligate DNA strands $\{G\}$ which are about twice as long as the $\{F\}$ oligomers ligated to the 3' termini of the matrix strands, and which are complementary in their 3' halves to the $\{F\}$ oligomers. The $\{G\}$ strands and the $\{X_j\}$ strands are ligated using bridging linker oligomers having the structure:

     (I), and

     (J), where h is about 6–9, with the h nucleotides at the 3' ends of the bridging linker strands being complementary to the last h nucleotides at the 3' ends of the $\{G\}$ strands. The bridging linkers (I) and (J) hybridize to the 3' terminal portions of the $\{G\}$ strands and the 5' terminal portions of the $\{X_j\}$ or $\{\underline{X}_j\}$ strands and align them end-to-end for efficient ligation to obtain strands of the form $\{G\}\{X_j\}$ and $\{GE\}\{\underline{X}_j\}$, respectively, which are purified from the shorter bridging linker oligomers.

(III) One of the resulting two strand collections, $\{G\}\{\underline{X}_j\}$ is incubated with a sample of the matrix strands and an enzyme with ligase activity, plus the set of (r+3)-mers:

     (K), and

     (L).

Figure 5:
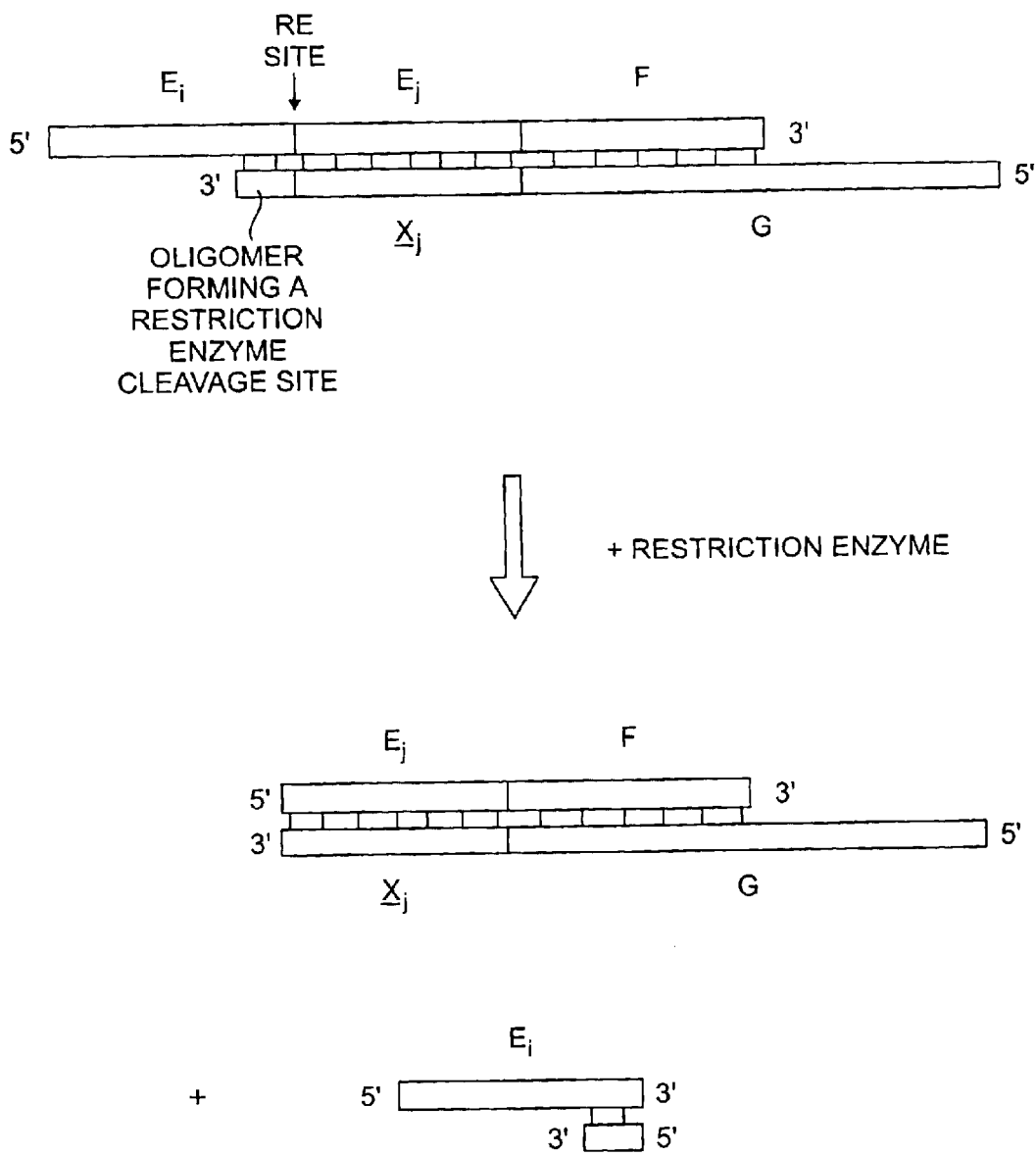
FIG. 5 schematically represents steps in the determination of the product of vector X and matrix $T_{ij}$, the outer product of $V_i V_j$, in which DNA strands containing $\{X_j\}$ are used to select $\{V_i\}$ strands of the form $\{E_i\}$ and $\{\underline{E}_i\}$ representing an unchanged sign contribution to the product. The abbreviation RE stands for restriction enzyme.

Ligation of the (r+3)-mers to the 3' ends of the $\{G\}\{\underline{X}_j\}$ strands that are hybridized to matrix strands results in formation of double-stranded recognition sites for the restriction enzyme Bst1107 I. The ligase is then inactivated, and the newly formed double-stranded restriction enzyme recognition sites are cut using Bst1107 I enzyme, resulting in release of a set of $\{V_i\}$ strands from the matrix strands (FIG. 5). Purification of the short $\{V_i\}$ segments yields a collection of $\{V_i\}$ strands of the form $\{E_i\}$ and $\{\underline{E}_i\}$ representing an unchanged sign contribution to the product.

Figure 6:
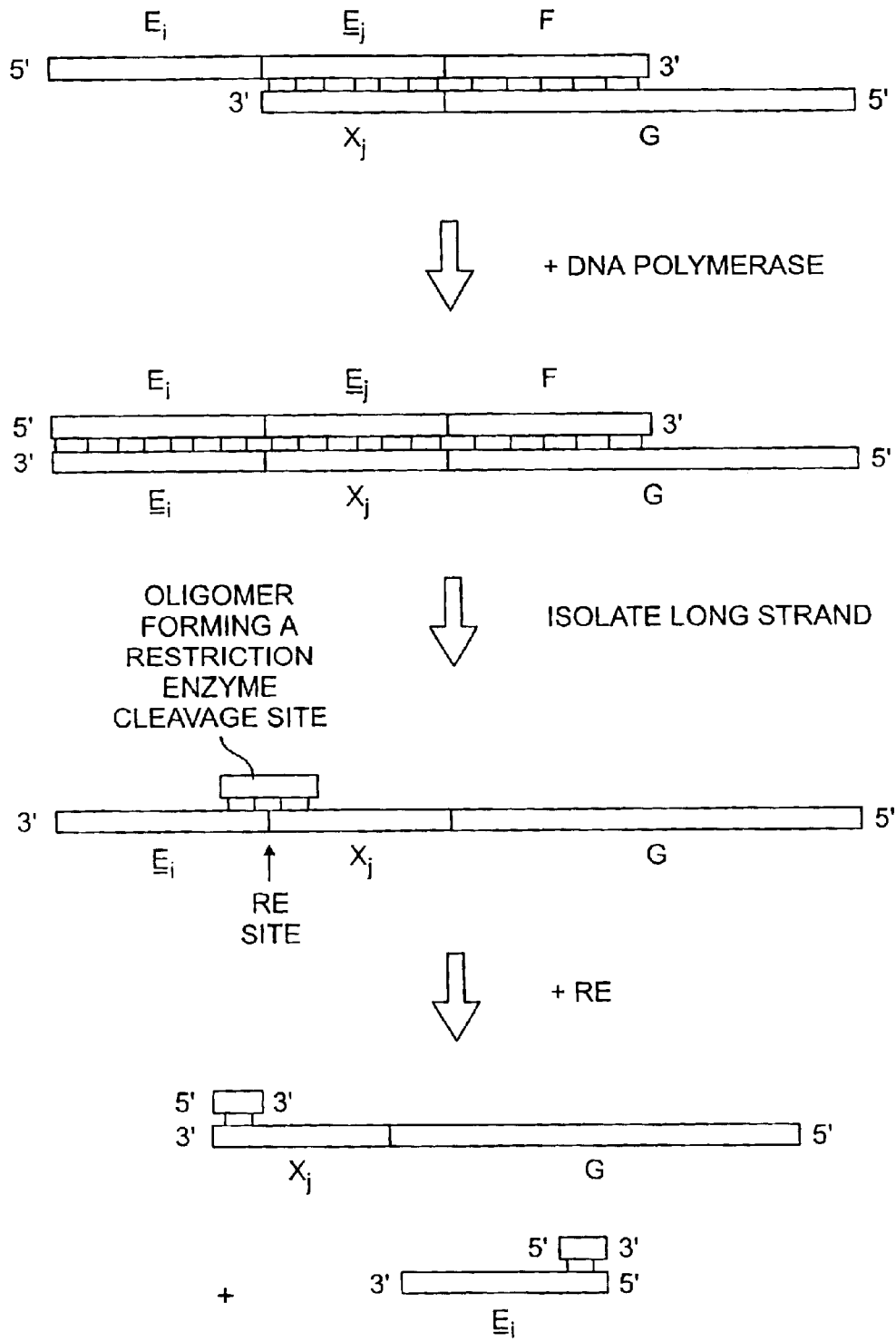
FIG. 6 schematically represents steps in the determination of the product of vector X and matrix $T_{ij}$ in which DNA strands containing $\{\underline{X}_j\}$ are used to select $\{\underline{V}_i\}$ strands of the form $\{E_i\}$ and $\{\underline{E}_i\}$ representing a changed sign contribution to the product.

(IV) A second sample of the matrix is treated to modify the 3' ends of the strands so that additional nucleotides cannot be attached in a polymerase-catalyzed extension reaction. For example, dideoxynucleotides can be added to the 3' termini of the V and W strands in a reaction catalyzed by a terminal transferase, as discussed above in the description of determination of an inner product. The modified matrix strands are then incubated with the other of the two strand collections, {G}{$X_j$}, and a DNA polymerase capable of primer extension, e.g., T4 DNA polymerase, in a buffer solution suitable for polymerase-catalyzed primer extension. Incubation results in the extension of the {$X_j$} strands at their 3' ends, using the {$E_i$} and {$\underline{E}_i$} strands at the 5' ends of the matrix DNAs as templates, to produce strands of the form {G}{$X_j$}{$\underline{V}_i$}. The strands are melted and the longer {G}{$X_j$}{$\underline{V}_i$} segments are separated. These strands are then hybridized with the set of four linker strands (E), (F), (G), and (H) described above, and the resulting double-stranded restriction enzyme recognition sites are cut using Bst1107 I enzyme, resulting in release of a set of {$\underline{V}_i$} strands. The strands are separated, e.g., on the basis of their size, to yield a collection of {$\underline{V}_i$} strands of the form {$E_i$} and {$\underline{E}_i$} representing a changed sign contribution to the inner product (FIG. 6).

(V) The {$\underline{V}_i$} strands from step (IV) above are added to the {$V_i$} strands obtained in step (III) above, using the previously described vector addition routine, to give a set of single-stranded DNA oligomers that is an analog representation of the desired matrix inner product.

Product of two Matrices

Oliver [10] describes an analog method for obtaining the product of two matrices containing only positive numbers, the disclosure of which is incorporated herein by reference. The method taught by Oliver can readily be extended to include negative numbers represented by complementary oligomers as described above for other vector and matrix algebra methods, and can be modified so that the product matrix has the same form as the starting matrices. However, for the neural network applications, this operation is not useful because the nonlinear amplification does not commute with matrix multiplication.

Input and Output Using a Hybridization Array

Vector operations, including vector addition and vector algebra, represented by the interactions of selected sets of DNA strands as discussed above, are preferably carried out using DNA hybridization arrays to provide the sets DNA strands representing positive and negative vectors needed to solve a given problem, and to analyze the sets of DNA strands representing a solution to the problem. The preferred methods for "writing" vector data as sets of DNA strands, and for "reading" sets of DNA strands to derive the vector data they represent, employ DNA hybridization micro-arrays attached to one or more DNA chips. The heightened efficiencies with which DNA strands representing vectors can be provided and detected using DNA chips permit practical implementation of the methods of the present invention in making a DNA computer.

A general method for "writing" digital data corresponding to an m-component vector V into analog form as a set of DNA strands $E_i$ and $\underline{E}_i$, wherein the DNA strands representing V are released from a DNA chip serving as an oligomer storing device, has been described above. Double-stranded DNA complexes of selected oligomer-storing depots in a micro-array on a DNA chip are locally denatured, e.g., by localized heating, and the desired soluble oligomers are collected from the solution in contact with the storage micro-array (see FIG. 2).

In the following examples, digital data in the form of an image of n×n picture elements, or pixels, is written, i.e., it is converted to analog information in the form of a set of DNA strands. The analog information is then read, i.e., it is converted back into image form. Although the example below demonstrates "writing" and "reading" image data, other types of data could just as readily be assigned to the vector DNA strands and interconverted from digital to analog form and back again in a similar manner. Since image data is being stored, the individual depot sites in the DNA micro-array are referred to as "pixels" in the following example.

(A) A set of DNA strands $E_i$ and $\underline{E}_i$ representing vector V that corresponds to digital data in the form of an image of n×n picture elements is provided as follows:

A DNA chip is obtained which supports a micro-array of oligomer depot sites, or pixels, at which are anchored single-stranded DNA oligomers having unique nucleotide sequences of from about 10 to 100 or more nucleotides in length, where there is a 1:1 correspondence between the maximum image size of n×n pixels and the number of pixel sites in the micro-array at which single-stranded oligomers are tethered, and where the micro-array includes a set of pixel sites at which are anchored single-stranded DNA oligomers that are complementary to the DNA strands of $E_i$ and $\underline{E}_i$. The pixel array supported by the DNA chip can comprise from about $10^2$ to $10^7$ or more pixels sites, at which are anchored as many different types of DNA oligomers. The pixels of the micro-array can have a diameter of from 4 to 50 $\mu$m or more, and the density of the single-stranded DNA oligomers anchored at each pixel site is about $10^4$ DNA molecules per $\mu m^2$. Saturating amounts of DNA strands complementary to the single-stranded DNA oligomers tethered to the pixels of the micro-array are then hybridized to the pixel array.

(B) Each data image is flashed on the DNA micro-plate using focused radiant energy, e.g., from an argon laser, so as to cause local heating that melts a portion of the double-stranded DNA at a specific set of pixel sites that corresponds to the particular set of pixels which make the image. The single-stranded DNA oligomers released by melting of the duplex oligomers at each heated pixel yield a number $n_1$ of $E_i$ or $\underline{E}_i$ molecules proportional to the image intensity at that pixel. By calibrating the relationship between the amount of radiant energy applied and the number of DNA molecules of a given sequence that are released, several bits of analog amplitude information about the image can be encoded into the concentrations of each of the $E_i$ or $\underline{E}_i$ oligomers collected.

(C) The micro-plate is washed and the set of DNA oligomers that was released by heating the selected pixels is collected. The total number of collected DNA molecules that represent a data image is N=$\Sigma n_i$. To subtract the average image intensity, as needed for orthogonality, add N/2 molecules randomly distributed over the complete set of $E_i$, using the vector addition algorithm. In working with real images, it may be desirable to use a micro-array having only $E_i$ (positive) strands. The set of DNA strands can be amplified, e.g. by PCR, and then separated from the amplification primers, when it is desirable to have more copies of each DNA strand than are obtained directly from the micro-array by the above method.

The inverse step of "reading" involves incubating a liquid sample containing the set of DNA oligomers that represents the data with a DNA chip supporting a pixel micro-array of single-stranded oligomers; i.e., a DNA array from which all non-covalently attached oligomers are stripped. The methodological steps and reaction conditions used for hybridizing the DNA oligomers representing the data to their complementary strands in the pixel array are essentially the same as those used for saturating the array with oligomers as discussed above. The quantity of different DNA oligomers captured at each pixel of the micro-plate is proportional to the concentration of the DNA oligomers in solution, for a short enough exposure, and can be determined by exposing the micro-plate to a solution of ethidium bromide and detecting the fluorescence emitted by ethidium bromide bound to the double-stranded DNA molecules in the pixel array on the micro-plate surface. One skilled in the art would appreciate that the image corresponding to the set of pixels containing double-stranded complexes can readily be obtained by using other reporter molecules that emit a detectable signal indicating formation of double-stranded complexes in the array; e.g., a flourescent reporter group can be attached directly to each of the data oligomers prior to incubating with the read-out micro-plate (for example, see [20] col. 10–11; [22]col. 20 lines 40–51; [23] page 40; [28] pages 28–30; [29] page 5024; [37] col. 5, line 16, to col. 6, line 56; and [38]). Alternatively, other detection methods, such as mass spectroscopy, are known and can be used for identifying the sites on a DNA chip that contain double-stranded complexes (for example, see [28] page 30]).

Since the rate of hybridization of the soluble oligomers to their tethered complements is proportional to the concentration of the soluble oligomers, the set of soluble DNA strands can be amplified, e.g. by PCR, prior to hybridizing to the chip in order to increase the rate of hybridization, and to give a stronger overall signal.

Implementation of a Hopfield Neural Network
Memorization and Recall

The present invention also includes methods for DNA analog representation of a neural network that make practical use of the massive parallelism possible with nucleic acid computing [1, 2, 11]. The invention implements a neural network by using DNA oligomers having selected nucleotide sequences representing positive and negative vectors as the neurons; by letting diffusion, specific hybridization of complementary oligomer sequences, and nucleotide sequence-specific reactions of DNA-modifying enzymes, as employed in the analog vector operations discussed above, serve as the connections and signaling between neurons; and by using hybridization to an array of single-stranded DNA oligomers having selected nucleotide sequences as a saturating function that gives, after one or more iterations, the output signal corresponding to the input activity [Penny et al. in [8], pages 386–387]. As an illustrative example, the present invention is described in its implementation as a DNA-based representation of a Hopfield neural network, which may be used to make an associative or content addressable memory [3].

As described by Hopfield [3], elements of memory are represented as m-component vectors $V = \Sigma_i V_i e_i$ (Equation 1). The items of experience, e.g., data sets or images, represented by a set of vectors $V_i^a$ are stored in memory by forming the outer product over all the experience vectors for $i \neq j$:

$$T_{ij} = \Sigma_a V_i^a V_j^a \quad (4),$$

The condition $T_{ii}=0$ is required along with $T_{ij}=T_{ji}$ for unconditional stability [39]. Recall of a particular experience $V_i^b$ imperfectly represented as $U_i^b$ is effected by the algorithm $$V_i = S(\Sigma T_{ij} V_j + U_i^b) \quad (5),$$

where the function $S(x)$ is a saturating function acting separately on each component of the vector $\Sigma T_{ij} V_j + U_i^b$. The statement that $S(x)$ is a saturating function means that $S(x)$ is one of class of functions $S(x)$ that are monotonically increasing with x and that have a maximum and a minimum value, respectively, for large and small values of x. Such functions include, for example, $\tan h(x)$, $x/\sqrt{a+x^2}$, x/nth root of $(a+x^n)$ where n is even, and the step function $S=-1$ for $x<0$, $S=1$ for $x>0$. In practice, $S(x)$ includes an additional term g that represents the small-signal gain; for example, $S(x) = g \cdot \tan h(x)$. Solutions to Equation 5 are typically found by iteration starting with $V_j=0$, with the small gain g being adjusted to facilitate convergence. If the $V_i^a$ are sufficiently different, i.e. are part of a nearly orthogonal set, the system will settle into a state closely resembling $V_i^b$ after a sufficient number of iterations of the method. Hopfield found that the number of memories that can be stored simultaneously is roughly 10% of the number of independent basis vectors.

Each vector $V = \Sigma V_i e_i$ in the neural network can be represented by a set of single-stranded DNA oligomers; e.g., by a set of (q+2r+6)-mers of the form $E_i$ (Equation 2) and $\underline{E}_i$ (Equation 3), representing positive and negative vectors, respectively, with concentrations $[E_i]$ proportional to the amplitudes $V_i$, as described above. A Hopfield neural network can be implemented as a content-addressable memory by a series of steps leading to identification of a complete image represented by an experience vector $V_i^b$, given an imperfectly represented vector $U_i^b$ that accurately contains a sufficient fraction of the information of the complete vector $V_i^b$. Using the methods of the invention, the complete $V_i^b$ vector can be recalled, given as little as a few ten-thousandths of the information contained in $V_i^b$. The number of iterations of the neural network algorithm needed to give convergence to the complete $V_i^b$ vector is reduced by using $U_i^b$ containing a greater portion of $V_i^b$.

Figure 7:
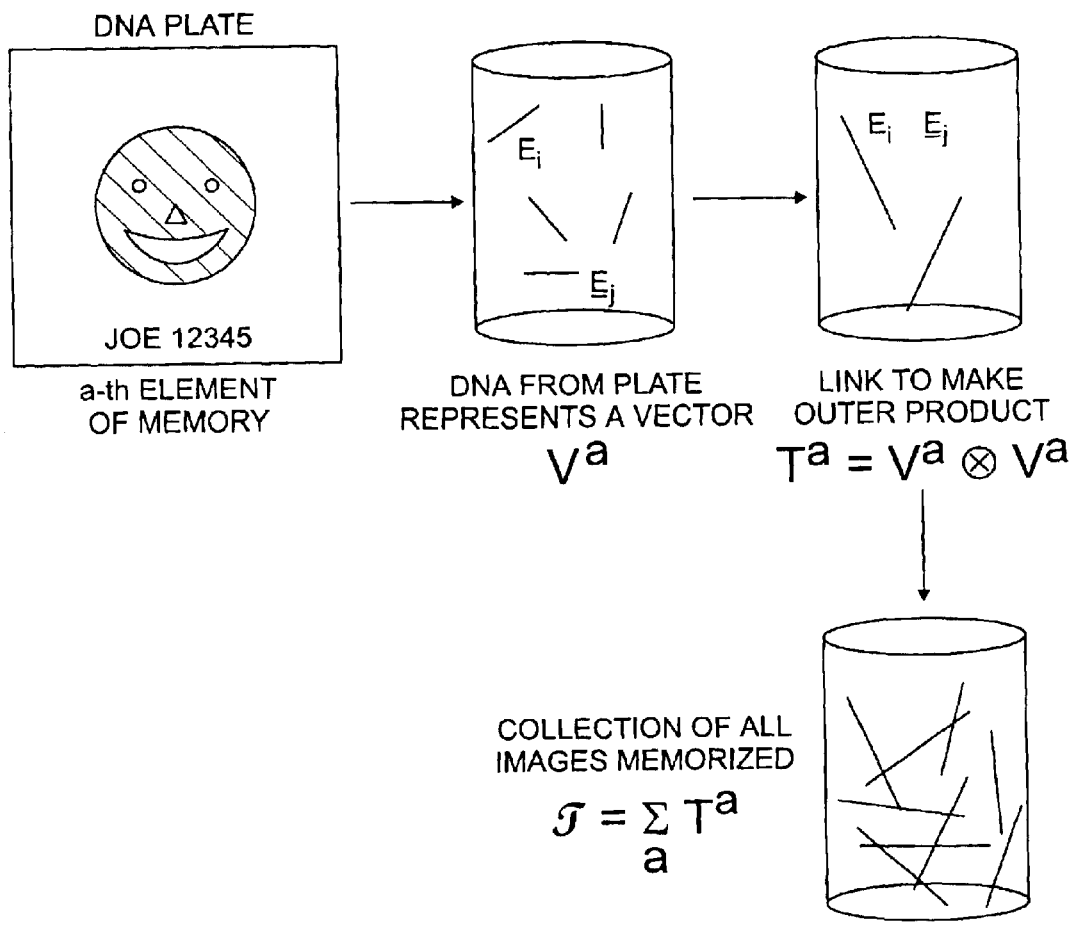
FIG. 7 schematically shows the "writing" of an image to memory. Following exposure of a DNA-saturated substrate, e.g., a DNA chip, to an image, with selective denaturation of double-stranded complexes at the image pixels, the oligomers that represent the image are collected. The image data is formed into an outer product, and the DNA strands representing all of the images to be stored are pooled to give the sum of the outer products, which is the memory matrix $T_{ij}$ of Eq. 2.

The memory matrix $T_{ij}$ defined in Equation (4) is the sum of all of the outer products $V_i^a V_j^a$ of all the experience vectors $V_i^a$ for $i \neq j$, and can be represented by forming and pooling all of the outer product DNA strands of the form $\{E_i\}\{E_j\}\{F\}$, $\{\underline{E}_i\}\{E_j\}\{F\}$, $\{E_i\}\{\underline{E}_j\}\{F\}$, and $\{\underline{E}_i\}\{\underline{E}_j\}\{F\}$, where $i \neq j$, for each experience vector $V_i^a$ (see FIG. 7).

Given a vector $U_i^b$ that imperfectly represents a particular experience $V_i^b$, the complete experience vector $V_i^b$ can be recalled from the content addressable memory, as depicted in Equation 5, by finding a set of DNA strands $X_i$ corresponding to the inner product of the $T_{ij}$ matrix and the vector $U_i^b$, and then implementing the saturating function $S(X_i)$, by which a selected set of DNA strands representing the vector $X_i$ is captured by hybridizing to a complete, sub-stoichiometric set of single-stranded $E_i$ and $\underline{E}_i$ strands. The set of $E_i$ and $\underline{E}_i$ strands used to apply the saturating function can be anchored to a solid support such as a set of beads, a polymeric matrix (e.g., in a chromatography column), or a silicon or $Al_2O_3$ chip, or they can be free in solution, e.g. with each saturating oligomer being linked to a ligand or an additional oligomer to facilitate isolation of the set of $X_i$ strands selected by the saturating reaction. The unhybridized, single-stranded $X_i$ strands are then washed away or are otherwise separated from the double-stranded complexes formed by hybridizing the $X_i$ strands to the set of saturating $E_i$ and $\underline{E}_i$ strands, and a set of oligomer strands representing the saturated $X_i$ strands, $S(X_i)$, is obtained by denaturing the duplex molecules containing the $S(X_1)$ strands, e.g. by heating, and collecting the selected set of single-stranded $X_i$ oligomers released by the denaturing treatment.

In a preferred embodiment, the single-stranded $E_i$ and $\underline{E}_i$ strands used to apply the saturating function are tethered to form a hybridization array on a DNA chip. The $X_i$ strands are hybridized to the sub-stoichiometric set of tethered $E_i$ and $\underline{E}_i$ strands, the hybridization array is then washed to remove excess $X_i$ strands, and a set of DNA strands representing the saturated $X_i$ strands, $S(X_i)$, is obtained by heating the duplex molecules of the hybridization array containing the $S(X_i)$ strands, and collecting the set of single-stranded DNA oligomers that are released by the denaturing treatment.

Following collection of the $S(X_i)$ strands, the steps corresponding to Equations (4) and (5) described above are reiterated by again applying the saturating function to the set of DNA strands corresponding to the inner product of the $T_{ij}$ memory matrix and the saturated $X_i$ vector. The information (e.g., the image) represented by the set of oligomer strands $S(X_i)$ produced by applying the saturating function to $X_i$ in one or more iterations can be derived by letting the selected set of $X_i$ oligomers hybridize to an array of complementary $E_i$ and $\underline{E}_i$ strands attached to a DNA chip, and detecting the double-stranded DNA molecules hybridized to the tethered oligomer array, in the same manner as described above for "reading" a set of DNA oligomers representing the solution to a vector operation. For example, by labeling the double-stranded complexes with ethidium bromide, or by labeling the $X_i$ oligomers with a fluorescing moiety before hybridizing to the DNA chip, and then by identifying the pixels that produce fluorescence upon illuminating the chip with light of the appropriate wavelength.

Figure 8:
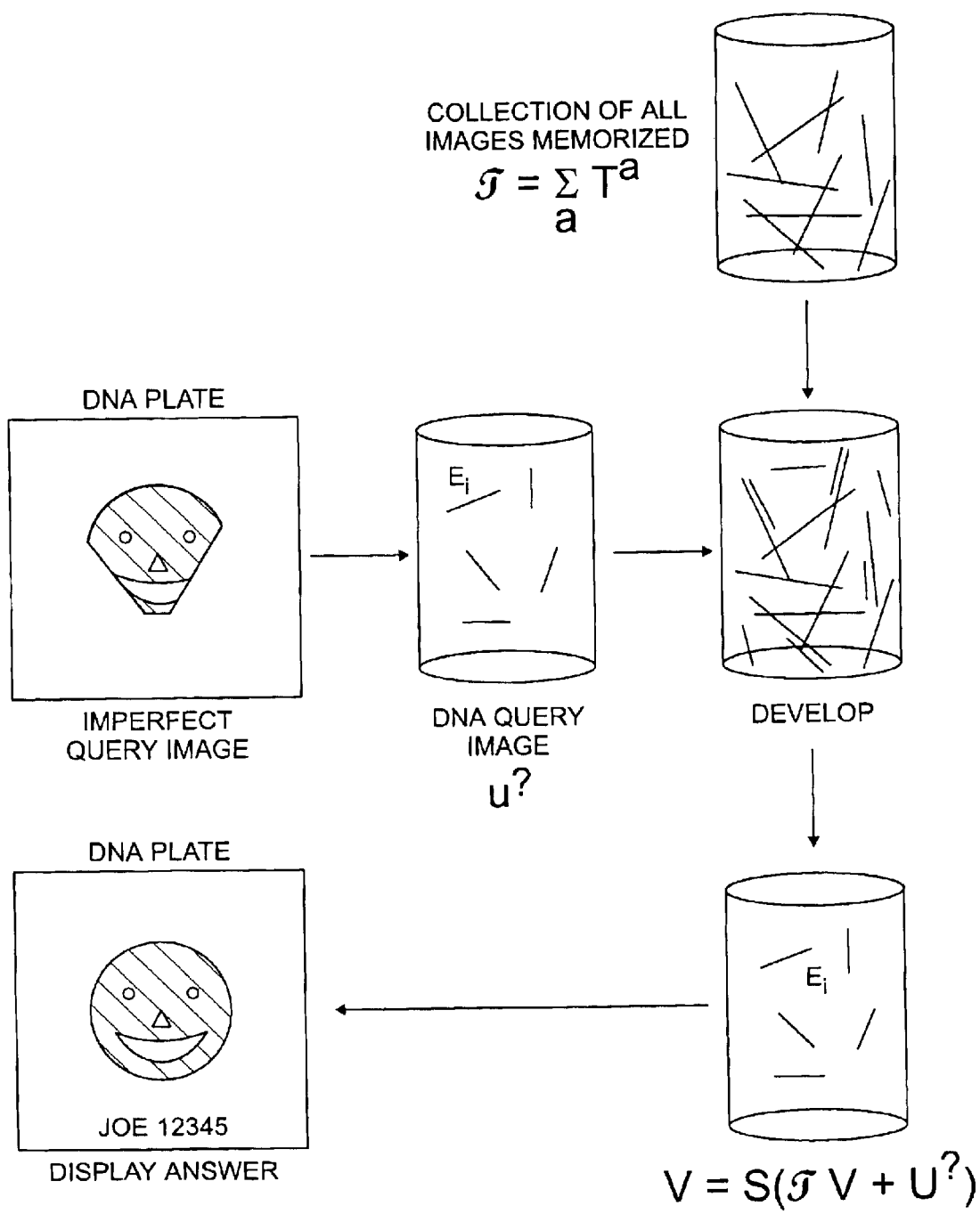
FIG. 8 schematically portrays retrieving a complete image from the memory matrix $T_{ij}$, starting with a set of DNA strands that represent $U_j$, a vector containing only a very small part of the image. A saturating function is applied to the set of DNA strands representing the product of the memory matrix $T_{ij}$ and the incomplete vector $U_j$ to yield a set of DNAs representing $X_i$. Iterations of the method continue until a set of DNA strands is obtained that represents the complete image.

To promote rapid convergence to obtain an image or data set consisting of binary data, i.e., of a series of 0s and 1s, it is preferred that the set of tethered $E_i$ and $\underline{E}_i$ strands that make up the hybridization array be sub-stoichiometric relative to the set of complementary $X_i$ strands, so that the saturating function serves to equalize the number of different $E_i$ and $\underline{E}_i$ strands in the set of DNA strands representing $S(X_i)$ released from the micro-array. Depending on the length of the query vector, two or more iterations of Equations (4) and (5) are sufficient to force the mixture into a steady state answer to the query, which is attained when two successive iterations of the neural network process described above yield the same complete image or set of data (FIG. 8).

In the preferred method, the hybridization reactions associated with forming the inner products of $T_{ij}$ and $U_i^b$ or $X_i$ are carried out using concentrations of $U_i^b$ and $X_i$ oligomers that are 1–4 times as great as the concentration of the $T_{ij}$ oligomers, in order to reduce the time required for the hybridization reaction. Similarly, when applying the saturating function to $X_i$, saturation of the oligomer binding sites in the array occurs more rapidly when the $X_i$ strands are present in stoichiometric excess relative to the complementary strands in the array. The preferred method may therefore include a step of amplification of the DNA strands representing $U_i^b$ and $X_i$, e.g., by PCR, prior to the steps of forming the inner products of $T_{ij}$ and $U_i^b$ or $X_i$, or prior to applying the saturating function to $X_i$, in order to increase the rates of hybridization associated with each of these steps. Increasing the copy number of the $X_i$ oligomers by PCR amplification, or changing the concentration of $X_i$ oligomers required to saturate the binding sites on the hybridization plate, e.g., by altering the number of complementary oligomers tethered to the pixels of the DNA chip, correspond to adjusting the small-signal gain parameter g of the saturating function, as in $S(x) = g \cdot \tan h(x)$.

Sample Volume

Each DNA strand representing an outer product matrix $V_i^a V_j^a$ is of the form $\{E_i\}\{E_j\}\{F\}$, and so is 80 nucleotides long when the basis vectors are represented by DNA strands of 32 nucleotides (q=20), and the F oligomers are 16 nucleotides long. A sample of memory $T_{ij}$ containing 10 copies of each of $10^4$ outer product records $V_i^a V_j^a$, where each vector $V_i^a$ is represented by up to $10^7$ basis vector 80-mer DNA strands, contains $10 \times 10^4 \times (10^7 \times 10^7) = 10^{19}$ DNA strands, and $80 \times 10^{19} = 8 \times 10^{20}$ nucleotides. The volume of such a sample of memory $T_{ij}$ for which the nucleotide concentration is 1 M is about 1.3 ml.

Query Time

The query time of the neural network algorithm is determined by the rate at which single stranded DNA oligomers representing the memory matrix $T_{ij}$ and the query vectors $U_i^b$ and $X_i$ of Equations (4) and (5) hybridize to form double-stranded DNAs. The rate of hybridization of complementary single-stranded DNA molecules is proportional to the total nucleotide concentration, and inversely proportional to the amount of unique nucleotide sequence in the DNA, and depends also on the ionic strength and temperature [30, 33]. Under a given set of temperature and ionic strength conditions, the hybridization rate can be accurately predicted when the number of copies of each DNA present in the solution are known [30–33]. For a solution containing $10^7$ different double-stranded nucleotide sequences and having a total nucleotide concentration=1 M, with temperature and ionic strength selected to be favorable for hybridization, the time required for one-half of the strands to re-hybridize following denaturation is about 580 seconds, about 10 minutes.

Feed-Forward Network

A multilayer feed-forward network with sigmoidal neuron response functions [7], for example $S(x) = \tan h(x)$, and at least one hidden layer of neurons, is able to represent at its output any continuous function of its inputs [40]. Such a network can be trained on known input-output pairs by the back-propagation of errors using an algorithm that is written in the language of matrix algebra [7]. A useful neural network of this type may thus be implemented with the analog vector algebra scheme outlined above; the learning algorithm involves multiplication by the derivative of the response function. Such a learning algorithm can be implemented by a network with one hidden layer with neuron outputs denoted $H_i$, an input layer with outputs $I_i$ and an output layer with outputs $O_i$, wherein the input and hidden layers are connected by weights $IH_{ij}$ and the hidden and output layers are connected by weights $HO_{ij}$. The equations for the network are thus $$H_i = S(\Sigma IH_{ij} I_j) \tag{7}$$

and $$O_i = S(\Sigma HO_{ij} H_j) \tag{8}.$$

The generalized back-propagation learning algorithm [7] is:
(1) Start with a set of random values for the weights.
(2) Present the network with a training stimulus $I_i^a$ having a desired $O_i^a$.
(3) Make changes to the HO weights $$\Delta HO_{ij} = \eta \Delta_i^{HO} H_j \tag{9},$$

where $$\Delta_i^{HO} = (O_i^a - O_i) S'(O_i) \tag{10},$$

and where $\eta$ is a learning rate parameter. The derivative $S'(X_i)$ of the sigmoidal function is proportional to the difference $S(X_i + \delta) - S(X_i - \delta)$ obtained by adding and subtracting a constant $\delta$ from all the components of $X_1$ before implementing the sigmoidal function S. The IH weights are changed according to $$\Delta IH_{ij} = \eta \Delta_i^{IH} I_j \quad (11)$$

where $$\Delta_i^{IH} = \Sigma \Delta_j^{HO} IH_{ji} S'(H_i) \quad (12)$$

The back-propagation algorithm is not very efficient, but constitutes a proof of principle for implementing a DNA version of a multilayer feedforward network.

Combined with new rapid techniques for the interconversion of digital data and analog DNA information, it should be possible to construct a DNA neural network having a cycle time of the order of an hour, and connectivity of the order of a few percent of the number of synapses of the human brain. While such a network could be imitated using a digital silicon super computer, one of the advantages of the molecular approach of the present invention is its small size and low price. On the other hand, an analog VLSI representation of a neural network on a single silicon chip is limited presently to less than about $10^8$ synapses. The disadvantages of using a non-solid state molecular computing device, for example, the time required to carry out the selection and synthesis of the necessary oligomers, and for biochemical steps such as separation of single-stranded from double-stranded oligomers, will disappear upon serious development of the various techniques involved in its implementation.

Baum has proposed using DNA operations such as those taught by Adleman [1] and Lipton [3] to produce an associative DNA memory of enormous capacity [11], as noted above. While the neural network design of the present invention would not exceed this capacity when used as an associative memory, it could also be configured in more general architectures for solving problems of prediction and classification [7, 40].

REFERENCES

[1] L. M. Adleman, "Molecular computation of solutions to combinatorial problems", Science 266, 1021 (1994).

[2] R. J. Lipton, "DNA solution of hard computational problems", Science 268, 542 (1995).

[3] J. J. Hopfield, "Neural networks and physical systems with emergent collective computational abilities", Proc. Nat. Acad. Sci. USA 79, 2554–2558 (1982); see for example, P. D. Wasserman, *Neural Computing, Theory and Practice*, Van Nostrand Reinhold, New York, 1989, ISBN 0-442-20743-3.

[4] L. D. Jackel, R. E. Howard, H. P. Graf, B. Straughn and J. S. Denker, "Artificial neural networks for computing", J. Vac. Sci. Technol. B4, 61 (1986).

[5] H. P. Graf, L. D. Jackel and J. S. Denker, "Analog electronic neural-networks for pattern recognition applications", in *Neural Networks: Concepts, Applications and Implementations*, Vol I, edited by V. Milutinovic and P. Antognetti, Prentice Hall, 1991, pages 155–179.

[6] See for example, P. D. Wasserman, *Neural Computing, Theory and Practice*, Van Nostrand Reinhold, New York, 1989, ISBN 0-442-20743-3.

[7] D. E. Rumelhart, G. E. Hinton and R. J. Williams, "Learning internal representations by error propagation", Chapter 8 of *Parallel Distributed Processing: Explorations in the Microstructure of Cognition*, edited by D. E. Rumelhart, J. L. McClelland et al., MIT Press, Cambridge, Mass., 1986, pages 318–362.

[8] For a tutorial on neural networks, see W. Penny and D. Frost, "Neural networks in clinical medicine", Medical Decision Making 16, 386–398 (1996).

See also the collection of articles in Computer 21(3) (1988):

B. D. Shriver, "Artificial neural systems", page 8;
T. Kohonen, "The neural phonetic typewriter", page 11;
B. Wilrow and R. Winter, "Neural nets for adaptive filtering and adaptive pattern recognition", page 25;
H. P. Graf, L. D. Jackel and W. E. Hubbard, "VLSI implementation of a neural network model, page 41;
J. Hutchinson, C. Koch, J. Luo and C. Mead, "Computing motion using analog and binary resistive networks", page 52;
K. Fukushima, "A neural network for visual pattern recognition", page 65;
G. A. Carpenter and S. Grossberg, "The ART of adaptive pattern recognition by a self-organizing neural network", page 77;
J. A. Feldman, M. A. Fanty and N. H. Goddard, "Computing with structured neural networks", page 91;
R. Linsker, "Self-organization in a perceptual network", page 105.

[9] F. Guarnieri, M. Fliss and C. Bancroft, "Making DNA add", Science 273, 220 (1996).

[10] J. S. Oliver, "Matrix multiplication with DNA", J. Molec. Evol 45, 161–167 (1997).

[11] E. B. Baum, "Building an associative memory vastly larger than the brain", Science 268, 583–585 (1995).

[12] R. Deaton, M. Garzon, R. C. Murphy, J. A. Rose, D. R. Franceschetti and S. E. Stevens Jr., "Reliability and efficiency of a DNA-based computation", Phys. Rev. Lett. 80, 417–420 (1998).

[13] Sambrook et al., 1989, *Molecular Cloning: A Laboratory Manual, Second Edition*, Books 1–3, Cold Spring Harbor Laboratory Press.

[14] B. Roe, J. Crabtree, and A. Kahn, 1996, *DNA Isolation and Sequencing: Essential Techniques*, John Wiley & Sons.

[15] J. M. Polak and James O'D. McGee, 1990, *In Situ Hybridization: Principles and Practice*, Oxford University Press.

[16] M. J. Gait (Editor), 1984, *Oligonucleotide Synthesis: A Practical Approach*, IRL Press.

[17] D. M. J. Lilley and J. E. Dahlberg, 1992, *Methods of Enzymology: DNA Structure Part A: Synthesis and Physical Analysis of DNA*, Methods in Enzymology, Vol. 211, Academic Press.

[18] J. D. Wilson, M. Gilman, J. Witkowski, and M. Zoller, 1992, *Recombinant DNA*, Second Edition, Scientific American Books.

[19] S. Agrawal, 1993, *Protocols for Oligonucleotide Conjugates: Synthesis and Analytical Techniques* (Methods in Molecular Biology, Volume 26), edited by, Humana Press.

[20] G. McGraw et al., U.S. Pat. No. 5,412,087.

[21] S. Fodor et al., U.S. Pat. No. 5,445,934.

[22] M. Heller et al., U.S. Pat. No. 5,605,662.

[23] G. Ramsay, Nature Biotechnology, vol. 16, pages 40–44, 1998.

[24] R. Drmanac et al., Genomics 4, pages 114–128, 1989.

[25] C. Mirkin et al., Nature 382, pages 607–609, 1996.

[26] R. Corn, DNA Computing Overview, last modified Mar. 13, 1998, <httpp://www.corninfo.chem.wisc.edu/writings/DNA overview.html>

[27] C. Cantor et al., U.S. Pat. No. 5,503,980.

[28] Marshall et al., Nature Biotechnology 16, pages 27–31, 1998.

[29] A. C. Pease et al., P.N.A.S. 91, pages 5022–26, 1994.

[30] J. Marmur, R. Rownd and C. L. Schildkraut, Prog. Nucleic Acid Res. 1, 231, 1963.

[31] R. J. Britten, D. E. Graham and B. R. Neufeld, "Analysis of repeating DNA sequences by reassociation", Methods in Enzymology 29, part E, 363–418, 1974.
[32] J. G. Wetmur and N. Davidson, "Kinetics of renaturization of DNA", J. Molec. Biol. 31, 349, 1968.
[33] R. J. Britten and D. E. Kohne, "Repeated sequences in DNA", Science 161, 529–540, 1968.
[34] T. Kamins, *Polycrystalline Silicon for Integrated Circuit Applications,* 1988, Kluwer Academic Publications, Boston.
[35] Cleavage of DNA with the restriction enzyme Bst1107 I is carried out by incubating at 37° C. in pH 8.5 reaction buffer consisting of 100 mM KCl, 10 mM Tris-HCl and 10 mM $MgCl_2$. The enzyme is heat inactivated by incubating at 65° C. for 20 minutes. See New England Biolabs 96/97 catalog, page 55.
[36] Exonuclease III (*E. coli*) catalyzes the stepwise removal of mononucleotides from the blunt or recessed 3'-hydroxyl termini of duplex DNA. Digestion of DNA by Exonuclease III is carried out by incubating at 37° C. in 66 mM Tris-HCl and 0.66 mM $MgCl_2$ at a pH of 8.0. Exonuclease III can be inactivated by heating to 70° C. for 20 minutes. See New England Biolabs 1996/1997 catalog, page 86.
[37] R. Rava et al., U.S. Pat. No. 5,545,531.
[38] S. Tyagi et al., Nature Biotechnology 16, 49–53, 1998.
[39] M. A. Cohen and S. G. Grossberg, "Absolute stability of global pattern formation and parallel memory storage by competitive neural networks", IEEE Transactions on Systems, Man and Cybernetics 13, 815826 (1983).
[40] K. Funahashi, "On the approximate realization of continuous mappings by neural networks", Neural Networks 2, 183–192 (1989); also, K. Hornik, M. Stinchcombe and H. White, "Multilayer feedforward networks are universal approximators", ibid., 359–366.

We claim:

1. An analog, oligomer-based method for determining a mathematical result of carrying out an operation of vector or matrix algebra on input data, wherein single-stranded oligomers $E_i$ and $\underline{E}_i$ are a subset of all single-stranded oligomers and are each in 1:1 correspondence with the basis vectors $e_i$, =1, 2, ... m in an abstract m-dimensional vector space;

wherein a set of the oligomers Ei and $\underline{E}i$ represents an m-component vector $V=\Sigma_i V_i e_i$, wherein the $E_i$ and $\underline{E}_i$ oligomers have complementary nucleotide sequences, with the $E_i$ oligomers representing the i-th component of V for which the amplitude $V_i$ is positive, and the $\underline{E}_i$ oligomers representing the i-th component of V for which $V_i$ is negative; and wherein the concentration of each of the oligomers $E_i$ or $\underline{E}_i$ is proportional to the absolute value of the amplitude $V_i$ of the i-th component of V, the method comprising the steps of (1) obtaining a composition comprising at least one set of single-stranded oligomers $E_i$ and $\underline{E}_i$ representing the components of a vector, said composition comprising an oligomer representing a vector component with a positive amplitude and also comprising an oligomer representing a vector component with a negative amplitude, wherein the concentrations of the oligomers $E_i$ or $\underline{E}_i$ in the composition are proportional to the absolute values of the amplitudes of the components they represent, which composition represents input data; and (2) subjecting said composition to at least one physical or chemical treatment having an effect on said oligomers in said composition that is an analog representation of an operation of vector or matrix algebra, and (3) detecting the effect of said treatment on said oligomers in said composition to determine the analog result of carrying out said operation of vector or matrix algebra on said input data;

wherein said analog result of carrying out said operation of vector or matrix algebra on said input data is quantitatively dependent on the concentrations of said at least one set of single-stranded oligomers $E_i$ and $\underline{E}_i$ in said composition.

2. The method of claim 1, wherein the oligomers independently comprise subunits selected from the group consisting of deoxyribonucleotides, ribonucleotides, and analogs of deoxyribonucleotides or ribonucleotides; and any single oligomer comprises one or a combination of two or more of said different types of subunits.

3. The method of claim 2, wherein said at least one physical or chemical treatment in step (2) is selected from the group consisting of (a) changing the relative concentrations of the oligomers in said composition, (b) allowing complementary oligomers in said composition to hybridize to each other, (c) determining the concentration of double-stranded oligomers in the composition, (d) separating double-stranded oligomers from non-double-stranded oligomers in the composition, (e) measuring the rate of hybridization of complementary oligomers in, the composition, (f) ligating oligomers together, (g) adding oligomer subunits to an end, of an oligomer in an enzyme-catalyzed reaction, (h) using an oligomer as a template in synthesizing a complementary oligomer sequence in a polymerase catalyzed reaction, (i) phosphorylating or de-phosphorylating a 5' terminus of an oligomer, and (j) cleaving an oligomer with a restriction enzyme.

4. The method of claim 3 wherein said operation of matrix algebra is multiplication of a vector by a scalar, and said method comprises changing the total concentrations of said oligomers in said composition by a factor equivalent to the scalar by which the vector is multipled, thereby obtaining an oligomer-containing composition that represents the product of multiplying said vector by said scalar.

5. The method of claim 3 wherein said operation of matrix algebra is addition of vectors, and said method comprises obtaining, for each vector to be added, a set of single-stranded oligomers $E_i$; and $\underline{E}_i$; representing the components of the vector, wherein the concentrations of the oligomers $E_i$; and $\underline{E}_i$; are proportional to the absolute values of the amplitudes of the components they represent;

mixing together, for each vector to be added, an amount of the set of oligomers representing said vector that is normalized to be proportional to the sum of the absolute values of the amplitudes of the components of said vector;

allowing complementary oligomers in the resulting mixture to hybridize; and separating the fully hybridized, double-stranded oligomers from the resulting mixture of oligomers, thereby obtaining a set of non-double-stranded oligomers that represents the sum of the added vectors.

6. The method of claim 1 wherein said operation of matrix or vector algebra is determining the inner product of two vectors V and W, and said method comprises:

(i) obtaining for each vector V and W, sets of single-stranded oligomers $E_i$ and $\underline{E}_i$ representing the components of the vector, wherein the concentrations of the oligomers $E_i$ and $\underline{E}_i$ are proportional to the absolute values of the amplitudes of the components they represent; and also obtaining a set of single-stranded oligomers $E_i$ and $\underline{E}_i$ representing the components of vector $\underline{W}$ that are complementary to said oligomers representing vector W, wherein the relative concentrations of the oligomers representing $\underline{W}$ proportional to the concentrations of their complementary oligomers in W;

(ii) combining samples of the oligomer representing vector V with samples of the oligomers representing vectors W and W̲ in separate respective first and second reaction mixtures and measuring $R_+$ and $R_-$ rates of hybridization associated with the respective first and second mixtures, and obtaining a numerical value proportional to the inner product of the two vectors from a difference between said $R_+$ and $R_-$ rates of hybridization.

7. The method of claim 1, wherein said operation of matrix or vector algebra includes obtaining an outer product matrix of two vectors $V_j$ and $W_j$, wherein said step of subjecting comprises obtaining a set of dimeric, single-stranded oligomers to represent an outer product of vectors V and W, each of said dimeric oligomers comprising (i) a first single-stranded oligomer sequence selected from the group consisting of $E_i$ or $E̲_i$ for each i-th component of V which oligomer is joined at its 3' end to the 5' end of (ii) a second single-stranded oligomer sequence selected from the group consisting of $E_j$ or $E̲_j$ for each j-th component of W, wherein the step of detecting include determining the concentration of said dimeric oligomers comprising oligomer sequences corresponding to the i-th component of V and the j-th component of W, said concentration corresponding to said outer product matrix.

8. A method for obtaining a data set $V_i^b$ from an oligomer-based, content-addressable memory following input of a data set $U_i^b$ that represents a portion of $V_i^b$, wherein data elements in the form of m-component vectors $V=\Sigma_i V_i e_i$ are represented in the memory by a set of the oligomers $E_i$ and $E̲_i$ that are a subset of all single-stranded oligomers and are in 1:1 correspondence with the basis vectors $e_i$ for i=1, 2, . . . m in an abstract m-dimensional vector space;

wherein oligomers $E_i$ and $E̲_i$ have complementary nucleotide sequences, with $E_i$ oligomers representing the i-th component of V for which the amplitude $V_i$ is positive, and $E̲_i$ representing the i-th component of V for which $V_i$ is negative; and wherein the concentration of each of oligomers $E_i$ and $E̲_i$ is proportional to the absolute value of the amplitude $V_i$ of the i-th component of V;

the method comprising:

(a) preparing a content-addressable memory representing memory matrix $T_{ij}$ in which are stored data sets corresponding to vectors $V_i^a$ for a=1 to a=n, where i=1, 2, . . . m, wherein $T_{ij}$ is the sum of all of the outer products $V_i^a V_j^a$ for i≠j, the preparing of the memory representing the matrix $T_{ij}$;

comprising obtaining for each vector $V^a$ a set of dimeric single-stranded oligomers, each of which comprise a first single-stranded oligomer sequence selected from the group consisting of $E_i$ or $E̲_i$ for each i-th component of $V^a$ for i=1 to i=m, and further comprises a second single-stranded oligomer sequence selected from the group consisting of $E_j$ or $E̲_j$ for each j-th component of $V^a$ for j=1 to j=m, except for i=j; and then forming a memory pool of said sets of dimeric oligomers obtained for each vector $V^a$ for a=1 to a=n to form the set of oligomers of the content-addressable memory representing the matrix $T_{ij}$;

(b) combining said memory pool of dimeric oligomers with a set of oligomers representing partial data Set $U_i^b$ under conditions wherein oligomer sequences $E_i^b$ and $E̲_i^b$ of data set $U_i^b$ hybridize specifically to complementary sequences $E_j$ and $E̲_j$ present in said memory pool oligomers; and obtaining an isolated set of monomeric oligomer strands $X_i$ comprising the first single strand oligomer sequences $E_i$ and $E̲_i$ of said memory pool of dimeric single stranded oligomers that hybridized specifically to said $U_i^b$ oligomers, wherein said $X_i$ oligomers do not further comprise said $E_j$ and $E̲_j$ oligomers of the second single-stranded sequences of said memory pool oligomers that are complementary to said $U_j^b$ oligomers;

(c) combining said set of $X_i$ oligomers with a set of single-stranded saturating oligomers comprising a set of $E_i$ and $E̲_i$ oligomers representing the complete set of basis vectors $e_i$ for i=1 to m, wherein the $E_i$ and $E̲_i$ oligomers are substoichiometric relative to said set of $X_i$ oligomers, in that the number of oligomers in the set of $X_i$ oligomers is greater than the number of saturating oligomers, so that complementary sequences hybridize to each other, denaturing the resulting duplex molecules, and isolating the subset of $X_i$ oligomer that hybridized specifically to said $E_i$ and $E̲_i$ sequences, to obtain a set of saturated $X_i$ strands, S(Xi);

(d) repeating steps (b) and (c) iteratively, using the set of saturated $X_i$ strands, $S(X_i)$ obtained in each previous implementation of step (c) as the set of oligomers representing partial data set $U_i^b$ employed in the subsequent implementation of step (b), until successive iterations yield the same set of oligomer strands $X_i$ produced by step (b) that represents data set $V_i^b$.

9. The method of claim 8, wherein the oligomers independently comprise subunits selected from the group consisting of deoxyribonucleotides, ribonucleotides, and analogs of deoxyribonucleotides or ribonucleotides; and any single oligomer comprises one or a combination of two or more of said different types of subunits.

10. The method of claim 8 wherein each of said oligomers forming said content addressable memory matrix $T_{ij}$ comprises, in order from the 5' end to the 3' end, (a) an oligomer strand comprising a nucleotide sequence representing an i-th component of V selected from the group consisting of $E_i$ and $E̲_i$ for i=1 to i=m, (b) an oligomer strand comprising a nucleotide sequence representing a j-th component of V selected from the group consisting of $E_j$ and $E̲_j$ for j=1 to j=m, wherein j≠i, and (c) a nucleotide sequence F that is not complementary to any sequence $E_i$ or $E̲_i$ for i=1 to i=m.

11. The method of claim 8 wherein said single-stranded oligomers comprising a complete, substoichiometric set of $E_i$ of step (c) and $E_i$ are anchored to a solid support.

12. The method of claim 11 wherein said solid support is contained in a chromatographic column.

13. The method of claim 11 wherein said solid support is, or is attached to, a silicon or $Al_2O_3$ chip.

* * * * *

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:  DNA based
      analog oligonucleotide

<400> SEQUENCE: 1
agctatcgat                                                              10

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:  DNA based
      analog oligonucleotide
<220> FEATURE:
<223> OTHER INFORMATION: the 3' end of this oligonucleotide is attached
      to about 3-6 oligomer subunits defined as S(r)...S(2)S(1)
      (complement) where r is the number of oligomer subunits.

<400> SEQUENCE: 2
aatgcaagat cgaaatttat acgtttatct tac                                    33

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:  DNA based
      analog oligonucleotide
<220> FEATURE:
<223> OTHER INFORMATION: the 3' end of this oligonucleotide is attached
      to about 3-6 oligomer subunits defined as R(1)R(2)...R(r) where r
      is the number of oligomer subunits.

<400> SEQUENCE: 3
aatgcaagat cgaaatttat acgtttatct tac                                    33

<210> SEQ ID NO 4
<211> LENGTH: 30
<212> TYPE: DNA
```

-continued

```
<213> ORGANISM: Artificial Sequence
<220> FEATURE:
<223> OTHER INFORMATION: Description of Artificial Sequence:  DNA based
      analog oligonucleotide

<400> SEQUENCE: 4
aatgcaagat cgaaatttat acgtttatct                                         30
```